US007144999B2

(12) United States Patent
Ward et al.

(10) Patent No.: US 7,144,999 B2
(45) Date of Patent: Dec. 5, 2006

(54) MODULATION OF HYPOXIA-INDUCIBLE FACTOR 1 ALPHA EXPRESSION

(75) Inventors: Donna T. Ward, Murrieta, CA (US); Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 569 days.

(21) Appl. No.: 10/304,126

(22) Filed: Nov. 23, 2002

(65) Prior Publication Data

US 2004/0101858 A1 May 27, 2004

(51) Int. Cl.

| | |
|---|---|
| ***C12Q 1/68*** | (2006.01) |
| ***C12P 19/34*** | (2006.01) |
| ***C12N 15/88*** | (2006.01) |
| ***C07H 21/02*** | (2006.01) |
| ***C07H 21/04*** | (2006.01) |

(52) U.S. Cl. ........................ 536/24.5; 435/6; 435/91.1; 435/91.31; 536/23.1; 536/24.31; 536/24.33

(58) Field of Classification Search .................... 435/6, 435/91.1, 91.31, 455, 458, 375; 536/23.1, 536/24.5, 24.31, 24.33; 514/44

See application file for complete search history.

(56) References Cited

U.S. PATENT DOCUMENTS

| | | | | |
|---|---|---|---|---|
| 5,882,914 | A | 3/1999 | Semenza | 435/252.3 |
| 6,060,458 | A * | 5/2000 | Moschel et al. | 514/44 |
| 6,133,246 | A * | 10/2000 | McKay et al. | 514/44 |
| 2004/0086498 | A9 | 5/2004 | Krissansen et al. | |
| 2004/0152655 | A1 | 8/2004 | Yoon et al. | 514/44 |
| 2004/0180357 | A1 | 9/2004 | Reich et al. | |
| 2005/0070474 | A1 | 3/2005 | Krissansen et al. | |
| 2005/0148496 | A1 | 7/2005 | Defranoux et al. | |
| 2005/0163781 | A1 | 7/2005 | Koninckx et al. | |

FOREIGN PATENT DOCUMENTS

| | | | |
|---|---|---|---|
| WO | WO 99/48916 | | 9/1999 |
| WO | WO 99/54500 | * | 10/1999 |
| WO | WO 03/085110 | A2 | 10/2003 |

OTHER PUBLICATIONS

Peracchi, A. et al., Rev. Med. Virol., vol. 14, pp. 47-64 (2004).*

Agrawal, S. et al., Molecular Med. Today, vol. 6, pp. 72-81 (2000).*

Chirila, T. et al., Biomaterials, vol. 23, pp. 321-342 (2002).*

Branch, A., Trends in Biochem. Sci. (TIBS), vol. 23, pp. 45-50 (1998).*

S. Crooke, Antisense Research & Application, Chapters 1 and 2, pp. 1-50, Ed. by S. Crooke, Publ. Springer-Verlag (1998).*

Andrew et al., *Nickel requires hypoxia-inducible factor-1 alpha, not redox signaling, to induce plasminogen activator inhibitor-1, Am J Physiol Lung Cell Mol Physiol*, 2001, 281:L607-615.

Caniggia et al., *Hypoxia-inducible factor-1 mediates the biological effects of oxygen on human trophoblast differentiation through TGFbeta*(3), *J. Clin. Invest*., 2000, 105:577-587.

Caniggia et al., *Oxygen and placental development during the first trimester: implications for the pathophysiology of pre-eclampsia, Placenta*, 2000, 21 Suppl A:S25-30.

Drutel et al., *Two splice variants of the hypoxia-inducible factor HIF-1alpha as potential dimerization partners of ARNT2 in neurons, Eur. J. Neurosci*., 2000, 12:3701-3708.

Furuta et al., *Hypoxia-inducible factor 1-dependent induction of intestinal trefoil factor protects barrier function during hypoxia, J. Exp. Med*., 2001, 193:1027-1034.

Huang et al., *Regulation of hypoxia-inducible factor 1alpha is mediated by an O2-dependent degradation domain via the ubiquitin-proteasome pathway, Proc. Natl. Acad. Sci. U. S. A.*, 1998, 95:7987-7992.

Iyer et al., *Cellular and developmental control of O2 homeostasis by hypoxia-inducible factor 1 alpha, Genes Dev*., 1998, 12:149-162.

Kakinuma et al., *Novel molecular mechanism of increased myocardial endothelin-1 expression in the failing heart involving the transcriptional factor hypoxia-inducible factor-1alpha induced for impaired myocardial energy metabolism, Circulation*, 2001, 103:2387-2394.

Maxwell et al., *Insights into the role of the von Hippel-Lindau gene product. A key player in hypoxic regulation, Exp. Nephrol*., 2001, 9:235-240.

Minchenko et al., *Hypoxia-inducible factor-1* (*HIF-1*) *mediated expression of the 6-phosphofructo-2-kinase/fructose-2, 6-bisphosphatase-3* (*PFKBF3*) *gene: its possible role in the Warburg effect, J. Biol. Chem*., 2001, 14:14.

Narravula et al., *Hypoxia-inducible factor 1-mediated inhibition of peroxisome proliferator-activated receptor alpha expression during hypoxia, J. Immunol*. 2001, 166:7543-7548.

Ravi et al., *Regulation of tumor angiogenesis by p53-induced degradation of hypoxia-inducible factor 1alpha, Genes Dev*., 2000, 14:34-44.

Ryan et al., *HIF-1 alpha is required for solid tumor formation and embryonic vascularization, Embo J*, 1998, 17:3005-3015.

Semenza, *HIF-1 and human disease: one highly involved factor, Genes Dev*., 2000, 14:1983-1991.

Semenza, *Hypoxia-inducible factor 1: control of oxygen homeostasis in health and disease, Pediatr. Res*., 2001, 49:614-617.

Sun et al., *Gene transfer of antisense hypoxia inducible factor-1 alpha enhances the therapeutic efficacy of cancer immunotherapy, Gene Ther*., 2001, 8:638-645.

(Continued)

*Primary Examiner*—Jane Zara
(74) *Attorney, Agent, or Firm*—Isis Pharmaceuticals, Inc. Patent Department

(57) ABSTRACT

Compounds, compositions and methods are provided for modulating the expression of hypoxia-inducible factor 1 alpha. The compositions comprise oligonucleotides, targeted to nucleic acid encoding hypoxia-inducible factor 1 alpha. Methods of using these compounds for modulation of hypoxia-inducible factor 1 alpha expression and for diagnosis and treatment of disease associated with expression of hypoxia-inducible factor 1 alpha are provided.

24 Claims, No Drawings

OTHER PUBLICATIONS

Sutter et al., *Hypoxia-inducible factor 1alpha protein expression is controlled by oxygen-regulated ubiquitination that is disrupted by deletions and missense mutations, Proc. Natl. Acad. Sci. U. S. A.*, 2000, 97:4748-4753.

Thrash-Bingham et al., *aHIF: a natural antisense transcript overexpressed in human renal cancer and during hypoxia, J. Natl. Cancer Inst.*, 1999, 91:143-151.

Wang et al., *Hypoxia-inducible factor 1 is a basic-helix-loop-helix-PAS heterodimer regulated by cellular O2 tension, Proc. Natl. Acad. Sci. U. S. A.*, 1995, 92:5510-5514.

Wang et al., *Purification and characterization of hypoxia-inducible factor 1, J. Biol. Chem.*, 1995, 270:1230-1237.

Yu et al., *Impaired physiological responses to chronic hypoxia in mice partially deficient for hypoxia-inducible factor 1alpha, J. Clin. Invest.*, 1999, 103:691-696.

Zagzag et al., *Expression of hypoxia-inducible factor 1alpha in brain tumors: association with angiogenesis, invasion, and progression, Cancer*, 2000, 88:2606-2618.

* cited by examiner

MODULATION OF HYPOXIA-INDUCIBLE FACTOR 1 ALPHA EXPRESSION

FIELD OF THE INVENTION

The present invention provides compositions and methods for modulating the expression of hypoxia-inducible factor 1 alpha. In particular, this invention relates to compounds, particularly oligonucleotide compounds, which, in preferred embodiments, hybridize with nucleic acid molecules encoding hypoxia-inducible factor 1 alpha. Such compounds are shown herein to modulate the expression of hypoxia-inducible factor 1 alpha.

BACKGROUND OF THE INVENTION

Oxygen homeostasis is an essential cellular and systemic function; hypoxia leads to metabolic demise, but this must be balanced by the risk of oxidative damage to cellular lipids, nucleic acids, and proteins resulting from hyperoxia. As a result, cellular and systemic oxygen concentrations are tightly regulated via response pathways that affect the activity and expression of a multitude of cellular proteins. This balance is disrupted in heart disease, cancer, cerebrovascular disease, and chronic obstructive pulmonary disease (Semenza, *Genes Dev.,* 2000, 14, 1983–1991).

The transcription factor hypoxia-inducible factor-1 (HIF-1) plays an essential role in homeostatic responses to hypoxia by binding to the DNA sequence 5'-TACGTGCT-3' and activating the transcription of dozens of genes in vivo under hypoxic conditions (Wang and Semenza, *J. Biol. Chem.,* 1995, 270, 1230–1237). These gene products participate in either increasing oxygen delivery to hypoxic tissues or activating an alternative metabolic pathway (glycolysis) which does not require oxygen. This list includes: aldolase C, enolase 1, glucose transporter 1, glucose transporter 3, glyceraldehyde-3-phosphate dehydrogenase, hexokinase 1, hexokinase 2, insulin-like growth factor-2 (IGF-2), IGF binding protein 1, IGF binding protein 3, lactate dehydrogenase A, phosphoglycerate kinase 1, pyruvate kinase M, p21, transforming growth factor B3, ceruloplasmin, erythropoietin, transferrin, transferrin receptor, a1b-adrenergic receptor, adrenomedullin, endothelin-1, heme oxygenase 1, nitric oxide synthase 2, plasminogen activator inhibitor 1, vascular endothelial growth factor (VEGF), VEGF receptor FTL-1, and p35 (Semenza, *Genes Dev.,* 2000, 14, 1983–1991). Expression of hypoxia-inducible factor-1 alpha is also sensitive to oxygen concentration: increased levels of protein are detected in cells exposed to 1% oxygen and these decay rapidly upon return of the cells to 20% oxygen (Wang et al., *Proc. Natl. Acad. Sci. U.S.A.,* 1995, 92, 5510–5514).

Hypoxia-inducible factor-1 alpha is a heterodimer composed of a 120 kDa alpha subunit complexed with a 91 to 94 kDa beta subunit, both of which contain a basic helix-loop-helix (Wang and Semenza, *J. Biol. Chem.,* 1995, 270, 1230–1237). The gene encoding hypoxia-inducible factor-1 alpha (also called HIF-1 alpha, HIF1A, HIF-1A, HIF1-A, and MOP1) was cloned in 1995 (Wang et al., *Proc. Natl. Acad. Sci. U.S.A.,* 1995, 92, 5510–5514). A nucleic acid sequence encoding hypoxia-inducible factor-1 alpha is disclosed and claimed in U.S. Pat. No. 5,882,914, as are expression vectors expressing the recombinant DNA, and host cells containing said vectors (Semenza, 1999).

Hypoxia-inducible factor-1 alpha expression and HIF-1 transcriptional activity are precisely regulated by cellular oxygen concentration. The beta subunit is a constitutive nuclear protein, while the alpha subunit is the regulatory subunit. Hypoxia-inducible factor-1 alpha mRNA is expressed at low levels in tissue culture cells, but it is markedly induced by hypoxia or ischemia in vivo (Yu et al., *J. Clin. Invest.,* 1999, 103, 691–696). Hypoxia-inducible factor-1 alpha protein is negatively regulated in non-hypoxic cells by ubiquitination and proteasomal degradation (Huang et al., *Proc. Natl. Acad. Sci. U.S.A.,* 1998, 95, 7987–7992). Under hypoxic conditions, the degradation pathway is inhibited, hypoxia-inducible factor-1 alpha protein levels increase dramatically, and the fraction that is ubiquitinated decreases. Hypoxia-inducible factor-1 alpha then translocates to the nucleus and dimerizes with a beta subunit (Sutter et al., *Proc. Natl. Acad. Sci. U.S.A.,* 2000, 97, 4748–4753).

A natural antisense transcript that is complementary to the 3' untranslated region of hypoxia-inducible factor-1 alpha mRNA has been discovered and is named "aHIF" (Thrash-Bingham and Tartof, *J. Natl. Cancer Inst.,* 1999, 91, 143–151). This is the first case of overexpression of a natural antisense transcript exclusively associated with a specific human malignant disease. aHIF is specifically overexpressed in nonpapillary clear-cell renal carcinoma under both normoxic and hypoxic conditions, but not in papillary renal carcinoma. Although aHIF is not further induced by hypoxia in nonpapillary disease, it can be induced in lymphocytes where there is a concomitant decrease in hypoxia-inducible factor-1 alpha mRNA.

Hypoxia-inducible factor-1 alpha plays an important role in promoting tumor progression and is overexpressed in common human cancers, including breast, colon, lung, and prostate carcinoma. Mutations that inactivate tumor supressor genes or activate oncogenes have, as one of their consequences, upregulation of hypoxia-inducible factor-1 alpha activity, either through an increase in hypoxia-inducible factor-1 alpha protein expression, hypoxia-inducible factor-1 alpha transcriptional activity, or both (Semenza, *Pediatr. Res.,* 2001, 49, 614–617).

Until a tumor establishes a blood supply, the hypoxic conditions limit tumor growth. Subsequent increases in hypoxia-inducible factor-1 alpha activity result in increased expression of target genes such as vascular endothelial growth factor (VEGF). VEGF expression is essential for vascularization and the establishment of angiogenesis in most solid tumors (Iyer et al., *Genes Dev.,* 1998, 12, 149–162). A significant association between hypoxia-inducible factor-1 alpha, VEGF overexpression and tumor grade is also seen in human glioblastoma multiforme, the highest grade glioma in which mean patient survival time is less than one year. The rapidly proliferating tumor outgrows its blood supply, resulting in extensive necrosis, and these regions express high levels of hypoxia-inducible factor-1 alpha protein and VEGF mRNA, suggesting a response of the tumor to hypoxia (Zagzag et al., *Cancer,* 2000, 88, 2606–2618).

The von Hippel-Landau (VHL) tumor supressor gene product is required for proteolytic destruction of the hypoxia-inducible factor-1 alpha subunit. Hydroxylation of a proline residue on the hypoxia-inducible factor-1 alpha subunit occurs under non-hypoxic conditions, and this is required for recognition by the VHL gene product. Consequently, individuals with errors in the VHL gene have a constitutive hypoxia-like phenotype. Individuals with this disease are predisposed to renal cysts, clear cell renal carcinoma, phaeochromocytoma, haemangioblastomas of the central nervous system, angiomas of the retina, islet cell tumors of the pancreas, and endolymphatic sac tumors (Maxwell et al., *Exp. Nephrol.,* 2001, 9, 235–240). Inactivation of the VHL tumor supressor, coupled with increased levels of hypoxia-inducible factor-1 alpha and VEGF, is responsible for the extensive vascularization of the haemangioblastoma brain tumor.

The p53 tumor supressor also targets hypoxia-inducible factor-1 alpha for degradation by the proteasome. Loss of p53 activity occurs in the majority of human cancers and indicates that amplification of normal hypoxia-inducible factor-1 alpha levels contributes to the angiogenic switch during tumorigenesis (Ravi et al., *Genes Dev.,* 2000, 14, 34–44).

A mouse model of pulmonary hypertension has shown that local inhibition of hypoxia-inducible factor-1 alpha activity in the lung might represent a therapeutic strategy for treating or preventing pulmonary hypertension in at risk individuals. In pulmonary hypertension hypoxia-induced vascular remodeling leads to decreased blood flow, which leads to progressive right heart failure and death. This hypoxia-induced vascular remodeling is markedly impaired in mice that are partially hypoxia-inducible factor-1 alpha deficient (Yu et al., *J. Clin. Invest.,* 1999, 103, 691–696). Decreased vascular density and retarded solid tumor growth is also seen in mouse embryonic stem cells which are deficient for hypoxia-inducible factor-1 alpha (Ryan et al., *Embo J,* 1998, 17, 3005–3015).

During hypoxia, cells shift to a glycolytic metabolic mode for their energetic needs and hypoxia-inducible factor-1 alpha is known to upregulate the expression of many glycolytic genes. Hypoxia-inducible factor-1 alpha may play a pivotal role in the Warburg effect in tumors, a paradoxical situation in which tumor cells growing under normoxic conditions show elevated glycolytic rates, which enhances tumor growth and expansion. Hypoxia-inducible factor-1 alpha mediates the expression of 6-phosphofructo-2-kinase/fructose-2,6-bisphosphatase-3, a gene whose protein product maintains levels of the key regulator of glycolytic flux, fructose-2,6-bisphosphate (Minchenko et al., *J. Biol. Chem.,* 2001, 14, 14).

Currently, there are no known therapeutic agents which effectively inhibit the synthesis of hypoxia-inducible factor-1 alpha and to date, investigative strategies aimed at modulating hypoxia-inducible factor-1 alpha function have involved the use of antisense expression vectors and oligonucleotides. These studies have served to define the involvement of hypoxia-inducible factor-1 alpha in disease progression and to identify novel roles of hypoxia-inducible factor-1 alpha in vivo including unique roles for hypoxia-inducible factor-1 alpha as a transcription factor under non-hypoxic conditions and as an inhibitor of gene expression.

Gene transfer of an antisense hypoxia-inducible factor-1 alpha plasmid has been shown to enhance the efficacy of cancer immunotherapy. Antisense therapy was shown to slow, but not eradicate, the growth of EL-4 tumors established in mice. In addition, endogenously expression of hypoxia-inducible factor-1 alpha was almost completely inhibited in these tumors. When antisense therapy was combined with T-cell costimulator B7-1 immunotherapy, the tumors completely and rapidly regressed within 1 week. Furthermore, when these tumor-free mice were rechallenged with EL-4 cells, no tumors emerged, indicating that systemic antitumor immunity had been achieved (Sun et al., *Gene Ther.,* 2001, 8, 638–645).

Activation of hypoxia-inducible factor-1 alpha is thought to aggravate heart failure by upregulation of cardiac ET-1, a gene product involved in heart failure and whose inhibition improves the survival rate of rats with heart failure. In a failing heart, a metabolic switch occurs, and hypoxia-inducible factor-1 alpha activates the expression of glycolytic enzymes as compensation for impaired b-oxidation of fatty acid. Another consequence of increased hypoxia-inducible factor-1 alpha activity is that in rat cardiomyocytes, hypoxia-inducible factor-1 alpha was shown to bind to the 5'-promoter region of the ET-1 gene and increase ET-1 expression. In vitro, an antisense oligonucleotide targeted to hypoxia-inducible factor-1 alpha largely inhibited the increased gene expression of ET-1, confirming the role of hypoxia-inducible factor-1 alpha in heart failure (Kakinuma et al., *Circulation,* 2001, 103, 2387–2394). This antisense oligonucleotide is comprised of 20 nucleotides and targets bases 11 to 31 of the rat hypoxia-inducible factor-1 alpha with GenBank accession number AF_057308.

Preeclampsia is a disorder of unknown etiology that is the leading cause of fetal and maternal morbidity and mortality. Defective downregulation of hypoxia-inducible factor-1 alpha may play a major role in the pathogenesis of preeclampsia. For most of the first trimester, the human fetus develops under hypoxic conditions but at 10–12 weeks the intervillous space opens, the fetus is exposed to maternal blood and at this stage the trophoblast cells invade the maternal decidua. The switch of the trophoblasts from a proliferative to an invasive phenotype is controlled by cellular oxygen concentration. The proliferative, non-invasive trophoblast phenotype appears to be maintained by hypoxia-inducible factor-1 alpha mediated expression of TGFbeta3 because treatment of human villous explants with an antisense oligonucleotide against hypoxia-inducible factor-1 alpha or TGF beta 3 induces invasion under hypoxic conditions. In this case the hypoxia-inducible factor-1 alpha antisense oligonucleotide was comprised of phosphorothioate oligonucleotides, 16 nucleotides in length, and targeted to the AUG codon (Caniggia et al., *J. Clin. Invest.,* 2000, 105, 577–587.; Caniggia et al., *Placenta,* 2000, 21 *Suppl A,* S25–30).

The human intestinal trefoil factor (ITF) gene product protects the epithelial barrier during episodes of intestinal hypoxia. The ITF gene promoter bears a binding site for hypoxia-inducible factor-1 alpha, and the function of hypoxia-inducible factor-1 alpha as a transcription factor for ITF was confirmed in vitro. T84 colonic epithelial cells were treated with a phosphorothioate antisense oligonucleotide, 15 nucleotides in length and targeted to the AUG codon of hypoxia-inducible factor-1 alpha and this resulted in a loss of ITF hypoxia inducibility (Furuta et al., *J. Exp. Med.,* 2001, 193, 1027–1034).

Human epidemiological and animal studies have associated inhalation of nickel dusts with an increased incidence of pulmonary fibrosis. Nickel transcriptionally activates plasminogen activator inhibitor (PAI-1), an inhibitor of fibrinolysis, through the hypoxia-inducible factor-1 alpha signaling pathway. This was evidenced by decreases in PAI-1 mRNA levels when human airway epithelial cells were treated with an antisense oligonucleotide directed against hypoxia-inducible factor-1 alpha identical to the one used in the preeclampsia study discussed above. These data may be critical for understanding the pathology of pulmonary fibrosis and other diseases associated with nickel exposure (Andrew et al., *Am J Physiol Lung Cell Mol Physiol,* 2001, 281, L607–615).

Hypoxia-inducible factor-1 alpha is constitutively expressed in cerebral neurons under normoxic conditions. A second dimerization partner for hypoxia-inducible factor-1 alpha is ARNT2, a cerebral translocator homologous to hypoxia-inducible factor-1 beta. One splice variant of hypoxia-inducible factor-1 alpha found in rat neurons dimerizes with ARNT2 more avidly than it does with HIF1b, and the resulting hypoxia-inducible factor-1 alpha-ARNT2 heterodimer does not recognize the hypoxia-inducible factor-1 alpha binding site of the erythropoietin gene. This suggests that transcription of a different set of genes is controlled by the hypoxia-inducible factor-1 alpha-ARNT2 heterodimer controls in neurons under nonhypoxic conditions than the hypoxia-inducible factor-1 alpha-hypoxia-inducible factor-1 alpha heterodimer controls under hypoxic conditions. This was evidenced by antisense oligonucleotide downregulation of hypoxia-inducible factor-1 alpha expression in which the antisense oligonucleotide consisted of 16 phosphorothioate nucleotides targeted to bases 38 to 54 of the rat hypoxia-inducible factor-1 with GenBank accession number AF_057308 (Drutel et al., *Eur. J. Neurosci.,* 2000, 12, 3701–3708).

A role for hypoxia-inducible factor-1 alpha in mediating a down-regulatory pathway was recently discovered using antisense oligonucleotide depletion of hypoxia-inducible factor-1 alpha. The peroxisome proliferator-activated receptors (PPARS) are a nuclear hormone-binding proteins that regulate transcriptional activities. Ligands which bind the PPAR-gamma isoform man amplify or inhibit the expression of inflammation-related gene products and may regulate the duration of inflammatory response. Hypoxia elicits a down-regulation of PPAR-gamma in intestinal epithelial cells which is effected through a binding site for hypoxia-inducible factor-1 alpha on the antisense strand of the PPAR-gamma gene. The expression of PPAR-gamma was upregulated in hypoxic cells when treated with an antisense oligonucleotide targeted to hypoxia-inducible factor-1 alpha identical to the one used in the preeclampsia study discussed above (Narravula and Colgan, *J. Immunol.,* 2001, 166, 7543–7548).

As a consequence of hypoxia-inducible factor-1 alpha involvement in many diseases, there remains a long felt need for additional agents capable of effectively inhibiting hypoxia-inducible factor-1 alpha function.

Antisense technology is emerging as an effective means for reducing the expression of specific gene products and may therefore prove to be uniquely useful in a number of therapeutic, diagnostic, and research applications for the modulation of hypoxia-inducible factor-1 alpha expression.

The present invention provides compositions and methods for modulating hypoxia-inducible factor-1 alpha expression.

SUMMARY OF THE INVENTION

The present invention is directed to compounds, especially nucleic acid and nucleic acid-like oligomers, which are targeted to a nucleic acid encoding hypoxia-inducible factor 1 alpha, and which modulate the expression of hypoxia-inducible factor 1 alpha. Pharmaceutical and other compositions comprising the compounds of the invention are also provided. Further provided are methods of screening for modulators of hypoxia-inducible factor 1 alpha and methods of modulating the expression of hypoxia-inducible factor 1 alpha in cells, tissues or animals comprising contacting said cells, tissues or animals with one or more of the compounds or compositions of the invention. Methods of treating an animal, particularly a human, suspected of having or being prone to a disease or condition associated with expression of hypoxia-inducible factor 1 alpha are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding hypoxia-inducible factor 1 alpha. This is accomplished by providing oligonucleotides which specifically hybridize with one or more nucleic acid molecules encoding hypoxia-inducible factor 1 alpha. As used herein, the terms "target nucleic acid" and "nucleic acid molecule encoding hypoxia-inducible factor 1 alpha" have been used for convenience to encompass DNA encoding hypoxia-inducible factor 1 alpha, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of hypoxia-inducible factor 1 alpha. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403–410; Zhang and Madden, *Genome Res.,* 1997, 7, 649–656).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611–620). Montgomery et al. have shown that the primary interference effects of dsRNA are posttranscriptional (Montgomery et al., *Proc. Natl. Acad. Sci. USA,* 1998, 95, 15502–15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806–811). Recently, it has been shown that it is, in fact, the single-stranded RNA oligomers of antisense polarity of the dsRNAs which are the potent inducers of RNAi (Tijsterman et al., *Science,* 2002, 295, 694–697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8–80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes hypoxia-inducible factor 1 alpha.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding hypoxia-inducible factor 1 alpha, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8–80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of hypoxia-inducible factor 1 alpha. "Modulators" are those compounds that decrease or increase the expression of a nucleic acid molecule encoding hypoxia-inducible factor 1 alpha and which comprise at least an 8-nucleobase portion which is complementary to a preferred target segment. The screening method comprises the steps of contacting a preferred target segment of a nucleic acid molecule encoding hypoxia-inducible factor 1 alpha with one or more candidate modulators, and selecting for one or more candidate modulators which decrease or increase the expression of a nucleic acid molecule encoding hypoxia-inducible factor 1 alpha. Once it is shown that the candidate modulator or modulators are capable of modulating (e.g. either decreasing or increasing) the expression of a nucleic acid molecule encoding hypoxia-inducible factor 1 alpha, the modulator may then be employed in further investigative studies of the function of hypoxia-inducible factor 1 alpha, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature,* 1998, 391, 806–811; Timmons and Fire, *Nature* 1998, 395, 854; Timmons et al., *Gene,* 2001, 263, 103–112; Tabara et al., *Science,* 1998, 282, 430–431; Montgomery et al., *Proc. Natl. Acad. Sci. USA,* 1998, 95, 15502–15507; Tuschl et al., *Genes Dev.,* 1999, 13, 3191–3197; Elbashir et al., *Nature,* 2001, 411, 494–498; Elbashir et al., *Genes Dev.* 2001, 15, 188–200). For example, such double-stranded moieties have been shown to inhibit the target by the classical hybridization of antisense strand of the duplex to the target, thereby triggering enzymatic degradation of the target (Tijsterman et al., *Science,* 2002, 295, 694–697).

The compounds of the present invention can also be applied in the areas of drug discovery and target validation. The present invention comprehends the use of the compounds and preferred target segments identified herein in drug discovery efforts to elucidate relationships that exist between hypoxia-inducible factor 1 alpha and a disease state, phenotype, or condition. These methods include detecting or modulating hypoxia-inducible factor 1 alpha comprising contacting a sample, tissue, cell, or organism with the compounds of the present invention, measuring the nucleic acid or protein level of hypoxia-inducible factor 1 alpha and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17–24; Celis, et al., *FEBS Lett.,* 2000, 480, 2–16), SAGE (serial analysis of gene expression) (Madden, et al., *Drug Discov. Today,* 2000, 5, 415–425), READS (restriction enzyme amplification of digested cDNAs) (Prashar and Weissman, *Methods Enzymol.,* 1999, 303, 258–72), TOGA (total gene expression analysis) (Sutcliffe, et al., *Proc. Natl. Acad. Sci. U.S.A.,* 2000, 97, 1976–81), protein arrays and proteomics (Celis, et al., *FEBS Lett.,* 2000, 480, 2–16; Jungblut, et al., *Electrophoresis,* 1999, 20, 2100–10), expressed sequence tag (EST) sequencing (Celis, et al., *FEBS Lett.,* 2000, 480, 2–16; Larsson, et al., *J. Biotechnol.,* 2000, 80, 143–57), subtractive RNA fingerprinting (SuRF) (Fuchs, et al., *Anal. Biochem.,* 2000, 286, 91–98; Larson, et al., *Cytometry,* 2000, 41, 203–208), subtractive cloning, differential display (DD) (Jurecic and Belmont, *Curr. Opin. Microbiol.,* 2000, 3, 316–21), comparative genomic hybridization (Carulli, et al., *J. Cell Biochem. Suppl.,* 1998, 31, 286–96), FISH (fluorescent in situ hybridization) techniques (Going and Gusterson, *Eur. J. Cancer,* 1999, 35, 1895–904) and mass spectrometry methods (To, *Comb. Chem. High Throughput Screen,* 2000, 3, 235–41).

The compounds of the invention are useful for research and diagnostics, because these compounds hybridize to nucleic acids encoding hypoxia-inducible factor 1 alpha. For example, oligonucleotides that are shown to hybridize with such efficiency and under such conditions as disclosed herein as to be effective hypoxia-inducible factor 1 alpha inhibitors will also be effective primers or probes under conditions favoring gene amplification or detection, respectively. These primers and probes are useful in methods requiring the specific detection of nucleic acid molecules encoding hypoxia-inducible factor 1 alpha and in the amplification of said nucleic acid molecules for detection or for use in further studies of hypoxia-inducible factor 1 alpha. Hybridization of the antisense oligonucleotides, particularly the primers and probes, of the invention with a nucleic acid encoding hypoxia-inducible factor 1 alpha can be detected by means known in the art. Such means may include conjugation of an enzyme to the oligonucleotide, radiolabelling of the oligonucleotide or any other suitable detection means. Kits using such detection means for detecting the level of hypoxia-inducible factor 1 alpha in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of hypoxia-inducible factor 1 alpha is treated by administering antisense compounds in accordance with this invention. For example, in one non-limiting embodiment, the methods comprise the step of administering to the animal in need of treatment, a therapeutically effective amount of a hypoxia-inducible factor 1 alpha inhibitor. The hypoxia-inducible factor 1 alpha inhibitors of the present invention effectively inhibit the activity of the hypoxia-inducible factor 1 alpha protein or inhibit the expression of the hypoxia-inducible factor 1 alpha protein. In one embodiment, the activity or expression of hypoxia-inducible factor 1 alpha in an animal is inhibited by about 10%. Preferably, the activity or expression of hypoxia-inducible factor 1 alpha in an animal is inhibited by about 30%. More preferably, the activity or expression of hypoxia-inducible factor 1 alpha in an animal is inhibited by 50% or more.

For example, the reduction of the expression of hypoxia-inducible factor 1 alpha may be measured in serum, adipose tissue, liver or any other body fluid, tissue or organ of the animal. Preferably, the cells contained within said fluids, tissues or organs being analyzed contain a nucleic acid molecule encoding hypoxia-inducible factor 1 alpha protein and/or the hypoxia-inducible factor 1 alpha protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No.

5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. “Chimeric” antisense compounds or “chimeras,” in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No.

6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N-4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylamino-oxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P═O) oligonucleotides are synthesized on an automated DNA synthesizer (Applied Biosystems model 394) using standard phosphoramidite chemistry with oxidation by iodine.

Phosphorothioates (P═S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12–16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820–11821; Matteucci, M. D. and Caruthers, M. H. *J. Am. Chem. Soc.,* 1981, 103, 3185–3191; Beaucage, S. L. and Caruthers, M. H. *Tetrahedron Lett.,* 1981, 22, 1859–1862; Dahl, B. J., et al., *Acta Chem. Scand,* 1990, 44, 639–641; Reddy, M. P., et al., *Tetrahedrom Lett.,* 1994, 25, 4311–4314; Wincott, F. et al., *Nucleic Acids Res.,* 1995, 23, 2677–2684; Griffin, B. E., et al., *Tetrahedron,* 1967, 23, 2301–2313; Griffin, B. E., et al., *Tetrahedron,* 1967, 23, 2315–2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 μM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12–16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]--[2'-deoxy]--[2'-O-(Methoxyethyl)] Chimeric Phosphorothioate Oligonucleotides

[2'-O-(2-methoxyethyl)]--[2'-deoxy]--[--2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Hypoxia-inducible Factor 1 Alpha In accordance with the present invention, a series of nucleic acid duplexes comprising the antisense compounds of the present invention and their complements can be designed to target hypoxia-inducible factor 1 alpha. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two-nucleobase overhang of deoxythymidine(dT) would have the following structure:

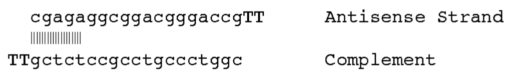

RNA strands of the duplex can be synthesized by methods disclosed herein or purchased from Dharmacon Research Inc., (Lafayette, Colo.). Once synthesized, the complementary strands are annealed. The single strands are aliquotted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate hypoxia-inducible factor 1 alpha expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12–16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 65–75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. Cells are treated and data are obtained in triplicate. After 4–7 hours of treatment at 37° C., the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Hypoxia-inducible Factor 1 Alpha Expression Antisense modulation of hypoxia-inducible factor 1 alpha expression can be assayed in a variety of ways known in the art. For example, hypoxia-inducible factor 1 alpha mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of hypoxia-inducible factor 1 alpha can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to hypoxia-inducible factor 1 alpha can be identified and obtained from a variety of sources, such as the MSRS catalog of antibodies (Aerie Corporation, Birmingham, Mich), or can be prepared via conventional monoclonal or polyclonal antibody generation methods well known in the art.

Example 11

Design of Phenotypic Assays and in vivo Studies for the Use of Hypoxia-inducible Factor 1 Alpha Inhibitors Phenotypic Assays Once hypoxia-inducible factor 1 alpha inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of hypoxia-inducible factor 1 alpha in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with hypoxia-inducible factor 1 alpha inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the hypoxia-inducible factor 1 alpha inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or hypoxia-inducible factor 1 alpha inhibitor. Furthermore, to prevent the doctors from being biased in treatments, they are not informed as to whether the medication they are administering is a hypoxia-inducible factor 1 alpha inhibitor or a placebo. Using this randomization approach, each volunteer has the same chance of being given either the new treatment or the placebo.

Volunteers receive either the hypoxia-inducible factor 1 alpha inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding hypoxia-inducible factor 1 alpha or hypoxia-inducible factor 1 alpha protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and hypoxia-inducible factor 1 alpha inhibitor treatment. In general, the volunteers treated with placebo have little or no response to treatment, whereas the volunteers treated with the hypoxia-inducible factor 1 alpha inhibitor show positive trends in their disease state or condition index at the conclusion of the study.

Example 12

RNA Isolation

Poly(A)+ mRNA Isolation

Poly(A)+ mRNA was isolated according to Miura et al., (*Clin. Chem.*, 1996, 42, 1758–1764). Other methods for poly(A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY96™ kit and buffers purchased from Qiagen Inc. (Valencia, Calif.) following the manufacturer's recommended procedures.

Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Hypoxia-inducible Factor 1 Alpha mRNA Levels Quantitation of hypoxia-inducible factor 1 alpha mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20–200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368–374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human hypoxia-inducible factor 1 alpha were designed to hybridize to a human hypoxia-inducible factor 1 alpha sequence, using published sequence information (GenBank accession number U29165.1, incorporated herein as SEQ ID NO:4). For human hypoxia-inducible factor 1 alpha the PCR primers were:

forward primer: CCAGTTACGTTCCTTCGATCAGT (SEQ ID NO: 5) reverse primer: TTTGAGGACT-TGCGCTTTCA (SEQ ID NO: 6) and the PCR probe was: FAM-TCACCATTAGAAAGCAGTTCCGCAAGCC-TAMRA (SEQ ID NO: 7) where FAM is the fluorescent dye and TAMRA is the quencher dye. For human GAPDH the PCR primers were: forward primer: GAAGGTGAAG-GTCGGAGTC(SEQ ID NO:8) reverse primer: GAAGATG-GTGATGGGATTTC (SEQ ID NO:9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Example 14

Northern Blot Analysis of Hypoxia-inducible Factor 1 Alpha mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human hypoxia-inducible factor 1 alpha, a human hypoxia-inducible factor 1 alpha specific probe was prepared by PCR using the forward primer CCAGTTACGT-TCCTTCGATCAGT (SEQ ID NO: 5) and the reverse primer TTTGAGGACTTGCGCTTTCA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Hypoxia-inducible Factor 1 Alpha Expression by Chimeric Phosphorothioate Oligonucleotides Having 2'-MOE Wings and a Deoxy Gap In accordance with the present invention, a series of antisense compounds were designed to target different regions of the human hypoxia-inducible factor 1 alpha RNA, using published sequences (GenBank accession number U29165.1, incorporated herein as SEQ ID NO: 4, positions 82000 to 139500 of the sequence with GenBank accession number AL137129.4, incorporated herein as SEQ ID NO: 11, GenBank accession number AU123241.1, incorporated herein as SEQ ID NO: 12, and GenBank accession number AB073325.1, incorporated herein as SEQ ID NO: 13). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines. The compounds were analyzed for their effect on human hypoxia-inducible factor 1 alpha mRNA levels by quantitative real-time PCR as described in other examples herein. Data are averages from three experiments in which A549 cells were treated with the antisense oligonucleotides of the present invention. If present, "N.D." indicates "no data".

Table 1

Inhibition of Human Hypoxia-inducible Factor 1 Alpha mRNA

TABLE 1

Inhibition of human hypoxia-inducible factor 1 alpha mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 175477 | Coding | 4 | 2496 | aaagtgatgtagtagctgca | 54 | 14 |
| 175418 | Coding | 4 | 854 | ggtatcatatacgtgaatgt | 73 | 15 |
| 175479 | 3'UTR | 4 | 3179 | taccacgtactgctggcaaa | 31 | 16 |
| 175480 | Coding | 4 | 2039 | tgtgctttgaggacttgcgc | 94 | 17 |
| 175481 | Coding | 4 | 583 | gaaatgtaaatcatgtcacc | 56 | 18 |
| 175482 | Coding | 4 | 1408 | tcaaagaggctacttgtatc | 75 | 19 |
| 175483 | Coding | 4 | 1674 | ttaatgcaacttcttgattg | 45 | 20 |

TABLE 1-continued

Inhibition of human hypoxia-inducible factor 1 alpha mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 175484 | 3'UTR | 4 | 3333 | atcattattatatgattaac | 60 | 21 |
| 175485 | 5'UTR | 4 | 152 | gaaaggcaagtccagaggtg | 42 | 22 |
| 175486 | 3'UTR | 4 | 3027 | taaactccctagccaaaaat | 40 | 23 |
| 175487 | Coding | 4 | 2085 | cattagcagtaggttcttgt | 75 | 24 |
| 175488 | 3'UTR | 4 | 3101 | gatcatgatgaaaggttact | 86 | 25 |
| 175489 | Coding | 4 | 1001 | aaatttcatatccaggctgt | 85 | 26 |
| 175490 | Coding | 4 | 460 | agtttcctcacacgcaaata | 38 | 27 |
| 175491 | Coding | 4 | 1983 | actgatcgaaggaacgtaac | 87 | 28 |
| 175492 | Coding | 4 | 2404 | cgctttctctgagcattctg | 44 | 29 |
| 175493 | Coding | 4 | 649 | aaatcaaacacactgtgtcc | 79 | 30 |
| 175494 | Coding | 4 | 1139 | tcctttagtaaacatatcat | 71 | 31 |
| 175495 | Coding | 4 | 1442 | caaagttaaagcatcaggtt | 79 | 32 |
| 175496 | Coding | 4 | 1765 | ctagtgcttccatcggaagg | 37 | 33 |
| 175497 | 3'UTR | 4 | 3424 | aatgccacataccttctaga | 24 | 34 |
| 175498 | 5'UTR | 4 | 110 | tcgtgagactagagagaagc | 71 | 35 |
| 175499 | 3'UTR | 4 | 3094 | atgaaaggttactgccttct | 81 | 36 |
| 175500 | Coding | 4 | 912 | tcagcaccaagcaggtcata | 8 | 37 |
| 175501 | 3'UTR | 4 | 2841 | aagtttgtgcagtattgtag | 33 | 38 |
| 175502 | Coding | 4 | 2396 | ctgagcattctgcaaagcta | 0 | 39 |
| 175503 | Coding | 4 | 350 | ttcagattctttacttcgcc | 54 | 40 |
| 175504 | Coding | 4 | 2320 | gataacacgttagggcttct | 41 | 41 |
| 175505 | Coding | 4 | 2331 | tcaaagcgacagataacacg | 51 | 42 |
| 175506 | Coding | 4 | 1091 | caaagcatgataatattcat | 56 | 43 |
| 175507 | Coding | 4 | 565 | ccatcatctgtgagaaccat | 86 | 44 |
| 175508 | Coding | 4 | 2222 | atatggtgatgatgtggcac | 76 | 45 |
| 175509 | 5'UTR | 4 | 51 | ctcctcaggtggcttgtcag | 33 | 46 |
| 175510 | 3'UTR | 4 | 2931 | tgagctgtctgtgatccagc | 94 | 47 |
| 175511 | Coding | 4 | 2321 | agataacacgttagggcttc | 86 | 48 |
| 175512 | Start Codon | 4 | 248 | catggtgaatcggtccccgc | 76 | 49 |
| 175513 | Coding | 4 | 1224 | tgttatatatgacagttgct | 73 | 50 |
| 224184 | Coding | 4 | 414 | ccttatcaagatgcgaactc | 63 | 51 |
| 224185 | Coding | 4 | 480 | ccaaatcaccagcatccaga | 32 | 52 |
| 224186 | Coding | 4 | 619 | aactgagttaatcccatgta | 72 | 53 |
| 224187 | Coding | 4 | 627 | ttagttcaaactgagttaat | 31 | 54 |
| 224188 | Coding | 4 | 706 | aggccatttctgtgtgtaag | 62 | 55 |

TABLE 1-continued

Inhibition of human hypoxia-inducible factor 1 alpha mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 224189 | Coding | 4 | 961 | ctatctaaaggaatttcaat | 10 | 56 |
| 224190 | Coding | 4 | 1036 | cccatcaattcggtaattct | 41 | 57 |
| 224191 | Coding | 4 | 1125 | tatcatgatgagttttggtc | 81 | 58 |
| 224192 | Coding | 4 | 1283 | aataataccactcacaacgt | 60 | 59 |
| 224193 | Coding | 4 | 1380 | caactttggtgaatagctga | 71 | 60 |
| 224194 | Coding | 4 | 1699 | agtgactctggatttggttc | 44 | 61 |
| 224195 | Coding | 4 | 1928 | catctccaagtctaaatctg | 36 | 62 |
| 224196 | Coding | 4 | 1995 | ctaatggtgacaactgatcg | 72 | 63 |
| 224197 | Coding | 4 | 2126 | cactgtttttaattcatcag | 65 | 64 |
| 224198 | Coding | 4 | 2457 | ataatgttccaattcctact | 31 | 65 |
| 224199 | Stop Codon | 4 | 2735 | agaaaaagctcagttaactt | 57 | 66 |
| 224200 | 3'UTR | 4 | 2828 | attgtagccaggcttctaaa | 68 | 67 |
| 224201 | 3'UTR | 4 | 3056 | atcttcttaaaaataattcg | 18 | 68 |
| 224202 | 3'UTR | 4 | 3193 | tgtgcaattgtggctaccac | 76 | 69 |
| 224203 | 3'UTR | 4 | 3316 | aacaatgtcatgttccaggt | 88 | 70 |
| 224204 | 3'UTR | 4 | 3486 | gctggcaaagtgactataga | 72 | 71 |
| 224205 | 3'UTR | 4 | 3896 | ttccacagaagatgtttatt | 30 | 72 |
| 224206 | 3'UTR | 4 | 3899 | tttttccacagaagatgttt | 14 | 73 |
| 224207 | intron | 11 | 11258 | tagagctaaacgatctagaa | 47 | 74 |
| 224208 | intron | 11 | 23630 | taactctttctggccttgaa | 93 | 75 |
| 224209 | intron | 11 | 25682 | attggccctaacagaaaatc | 19 | 76 |
| 224210 | intron: exon junction | 11 | 27616 | agaacttatcctacttaaca | 7 | 77 |
| 224211 | intron | 11 | 39357 | gtttccctcgtgttgctcag | 63 | 78 |
| 224212 | exon: intron junction | 11 | 39759 | ttgtacttactatcatgatg | 25 | 79 |
| 224213 | exon: intron junction | 11 | 41520 | acttacttacctcacaacgt | 9 | 80 |
| 224214 | intron: exon junction | 11 | 47989 | aatctgtgtcctttaaaaca | 35 | 81 |
| 224215 | exon | 11 | 2745 | tgtgcactgaggagctgagg | 19 | 82 |
| 224216 | exon | 4 | 296 | acgttcagaacttatctttt | 45 | 83 |
| 224217 | Stop Codon | 13 | 2221 | catgctaaataattcctact | 0 | 84 |

As shown in Table 1, SEQ ID NOs 14, 15, 17, 18, 19, 20, 21, 22, 23, 24, 25, 26, 28, 29, 30, 31, 32, 35, 36, 40, 41, 42, 43, 44, 45, 47, 48, 49, 50, 51, 53, 55, 57, 58, 59, 60, 61, 63, 64, 66, 67, 69, 70, 71, 74, 75, 78 and 83 demonstrated at least 40% inhibition of human hypoxia-inducible factor 1 alpha expression in this assay and are therefore preferred. More preferred are SEQ ID NOs 47, 48 and 25. The target regions to which these preferred sequences are complementary are herein referred to as "preferred target segments" and are therefore preferred for targeting by compounds of the present invention. These preferred target segments are shown in Table 2. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in hypoxia-inducible factor 1 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 90592 | 4 | 2496 | tgcagctactacatcacttt | 14 | *H. sapiens* | 85 |
| 90593 | 4 | 854 | acattcacgtatatgatacc | 15 | *H. sapiens* | 86 |
| 90595 | 4 | 2039 | gcgcaagtcctcaaagcaca | 17 | *H. sapiens* | 87 |
| 90596 | 4 | 583 | ggtgacatgatttacatttc | 18 | *H. sapiens* | 88 |
| 90597 | 4 | 1408 | gatacaagtagcctctttga | 19 | *H. sapiens* | 89 |
| 90598 | 4 | 1674 | caatcaagaagttgcattaa | 20 | *H. sapiens* | 90 |
| 90599 | 4 | 3333 | gttaatcatataataatgat | 21 | *H. sapiens* | 91 |
| 90600 | 4 | 152 | cacctctggacttgcctttc | 22 | *H. sapiens* | 92 |
| 90601 | 4 | 3027 | atttttggctagggagttta | 23 | *H. sapiens* | 93 |
| 90602 | 4 | 2085 | acaagaacctactgctaatg | 24 | *H. sapiens* | 94 |
| 90603 | 4 | 3101 | agtaacctttcatcatgatc | 25 | *H. sapiens* | 95 |
| 90604 | 4 | 1001 | acagcctggatatgaaattt | 26 | *H. sapiens* | 96 |
| 90606 | 4 | 1983 | gttacgttccttcgatcagt | 28 | *H. sapiens* | 97 |
| 90607 | 4 | 2404 | cagaatgctcagagaaagcg | 29 | *H. sapiens* | 98 |
| 90608 | 4 | 649 | ggacacagtgtgtttgattt | 30 | *H. sapiens* | 99 |
| 90609 | 4 | 1139 | atgatatgtttactaaagga | 31 | *H. sapiens* | 100 |
| 90610 | 4 | 1442 | aacctgatgctttaactttg | 32 | *H. sapiens* | 101 |
| 90613 | 4 | 110 | gcttctctctagtctcacga | 35 | *H. sapiens* | 102 |
| 90614 | 4 | 3094 | agaaggcagtaacctttcat | 36 | *H. sapiens* | 103 |
| 90618 | 4 | 350 | ggcgaagtaaagaatctgaa | 40 | *H. sapiens* | 104 |
| 90619 | 4 | 2320 | agaagccctaacgtgttatc | 41 | *H. sapiens* | 105 |
| 90620 | 4 | 2331 | cgtgttatctgtcgctttga | 42 | *H. sapiens* | 106 |
| 90621 | 4 | 1091 | atgaatattatcatgctttg | 43 | *H. sapiens* | 107 |
| 90622 | 4 | 565 | atggttctcacagatgatgg | 44 | *H. sapiens* | 108 |
| 90623 | 4 | 2222 | gtgccacatcatcaccatat | 45 | *H. sapiens* | 109 |
| 90625 | 4 | 2931 | gctggatcacagacagctca | 47 | *H. sapiens* | 110 |
| 90626 | 4 | 2321 | gaagccctaacgtgttatct | 48 | *H. sapiens* | 111 |
| 90627 | 4 | 248 | gcggggaccgattcaccatg | 49 | *H. sapiens* | 112 |
| 90628 | 4 | 1224 | agcaactgtcatatataaca | 50 | *H. sapiens* | 113 |
| 140838 | 4 | 414 | gagttcgcatcttgataagg | 51 | *H. sapiens* | 114 |

TABLE 2-continued

Sequence and position of preferred target segments identified in hypoxia-inducible factor 1 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 140840 | 4 | 619 | tacatgggattaactcagtt | 53 | *H. sapiens* | 115 |
| 140842 | 4 | 706 | cttacacacagaaatggcct | 55 | *H. sapiens* | 116 |
| 140844 | 4 | 1036 | agaattaccgaattgatggg | 57 | *H. sapiens* | 117 |
| 140845 | 4 | 1125 | gaccaaaactcatcatgata | 58 | *H. sapiens* | 118 |
| 140846 | 4 | 1283 | acgttgtgagtggtattatt | 59 | *H. sapiens* | 119 |
| 140847 | 4 | 1380 | tcagctattcaccaaagttg | 60 | *H. sapiens* | 120 |
| 140848 | 4 | 1699 | gaaccaaatccagagtcact | 61 | *H. sapiens* | 121 |
| 140850 | 4 | 1995 | cgatcagttgtcaccattag | 63 | *H. sapiens* | 122 |
| 140851 | 4 | 2126 | ctgatgaattaaaaacagtg | 64 | *H. sapiens* | 123 |
| 140853 | 4 | 2735 | aagttaactgagctttttct | 66 | *H. sapiens* | 124 |
| 140854 | 4 | 2828 | tttagaagcctggctacaat | 67 | *H. sapiens* | 125 |
| 140856 | 4 | 3193 | gtggtagccacaattgcaca | 69 | *H. sapiens* | 126 |
| 140857 | 4 | 3316 | acctggaacatgacattgtt | 70 | *H. sapiens* | 127 |
| 140858 | 4 | 3486 | tctatagtcactttgccagc | 71 | *H. sapiens* | 128 |
| 140861 | 11 | 11258 | ttctagatcgtttagctcta | 74 | *H. sapiens* | 129 |
| 140862 | 11 | 23630 | ttcaaggccagaaagagtta | 75 | *H. sapiens* | 130 |
| 140865 | 11 | 39357 | ctgagcaacacgagggaaac | 78 | *H. sapiens* | 131 |
| 140870 | 4 | 296 | aaaagataagttctgaacgt | 83 | *H. sapiens* | 132 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of hypoxia-inducible factor 1 alpha.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 16

Western Blot Analysis of Hypoxia-inducible Factor 1 Alpha Protein Levels

Western blot analysis (immunoblot analysis) is carried out using standard methods. Cells are harvested 16–20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to hypoxia-inducible factor 1 alpha is used, with a radiolabeled or fluorescently labeled secondary antibody directed against the primary antibody species. Bands are visualized using a PHOSPHORIMAGER™ (Molecular Dynamics, Sunnyvale Calif.)

What is claimed is:

1. An oligomeric compound 12 to 50 nucleobases in length targeted to a nucleic acid molecule encoding hypoxia-inducible factor 1 alpha (SEQ ID NO: 4), said compound comprising at least an 8-nucleobase portion of SEQ ID NO: 47, wherein said compound is 100% complementary to said nucleic acid molecule encoding hypoxia-inducible factor 1 alpha.

2. The compound of claim 1 wherein said compound is 15 to 30 nucleobases in length.

3. The compound of claim 1 wherein said compound is an oligonucleotide.

4. The compound of claim 3 wherein said compound is an antisense oligonucleotide.

5. The compound of claim 3 wherein said compound is a DNA oligonucleotide.

6. The compound of claim 3 wherein said compound is an RNA oligonucleotide.

7. The compound of claim 3 wherein said compound is a chimeric oligonucleotide.

8. The compound of claim 1 comprising at least one modified internucleoside linkage, sugar moiety, or nucleobase.

9. The compound of claim 1 comprising at least one 2'-O-methoxyethyl sugar moiety.

10. The compound of claim 1 comprising at least one phosphorothioate internucleoside linkage.

11. The compound of claim 1 comprising at least one 5-methylcytosine.

12. An antisense oligonucleotide 18, 19, 20, 21 or 22 nucleobases in length targeted to a nucleic acid molecule encoding hypoxia-inducible factor 1 alpha (SEQ ID NO: 4), said compound having at least 90% identity with SEQ ID NO: 47.

13. The antisense oligonucleotide of claim 12 which is 19, 20 or 21 nucleobases in length, said antisense oligonucleotide having at least 95% identity with SEQ ID NO: 47.

14. The antisense oligonucleotide of claim 12 which is a DNA oligonucleotide.

15. The antisense oligonucleotide of claim 12 which is an RNA oligonucleotide.

16. The antisense oligonucleotide of claim 12 which is a chimeric oligonucleotide.

17. The antisense oligonucleotide of claim 12 comprising at least one modified internucleoside linkage, sugar moiety, or nucleobase.

18. The antisense oligonucleotide of claim 12 comprising at least one 2'-O-methoxyethyl sugar moiety.

19. The antisense oligonucleotide of claim 12 comprising at least one phosphorothioate internucleoside linkage.

20. The antisense oligonucleotide of claim 12 comprising at least one 5-methylcytosine.

21. An antisense oligonucleotide 20 to 50 nucleobases in length targeted to a nucleic acid molecule encoding hypoxia-inducible factor 1 alpha (SEQ ID NO: 4), wherein the nucleotide sequence of said antisense oligonucleotide comprises SEQ ID NO: 47.

22. An antisense oligonucleotide wherein the nucleotide sequence of said antisense oligonucleotide consists of SEQ ID NO: 47.

23. The antisense oligonucleotide of claim 22 comprising a central region of ten 2'-deoxynucleotides which is flanked on each side by five 2'-O-methoxyethyl nucleotides, wherein the internucleoside linkages of said oligonucleotide are phosphorothioate throughout the oligonucleotide and the cytidine residues are 5-methylcytidines.

24. A pharmaceutical composition comprising the antisense oligonucleotide of claim 23.

* * * * *

SEQUENCE LISTING

```
<160> NUMBER OF SEQ ID NOS: 132

<210> SEQ ID NO 1
<211> LENGTH: 20
<212> TYPE: DNA
```

-continued

```
<213> ORGANISM: Artificial Sequence
<220> FEATURE:
<223> OTHER INFORMATION: Antisense Oligonucleotide

<400> SEQUENCE: 1

tccgtcatcg ctcctcaggg                                                20


<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2

gtgcgcgcga gcccgaaatc                                                20


<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3

atgcattctg cccccaagga                                                20


<210> SEQ ID NO 4
<211> LENGTH: 3933
<212> TYPE: DNA
<213> ORGANISM: H. sapiens
<220> FEATURE:
<221> NAME/KEY: CDS
<222> LOCATION: (265)...(2745)

<400> SEQUENCE: 4

cacgaggcag cactctcttc gtcgcttcgg ccagtgtgtc gggctgggcc ctgacaagcc     60

acctgaggag aggctcggag ccgggcccgg accccggcga ttgccgcccg cttctctcta    120

gtctcacgag ggtttcccg cctcgcaccc ccacctctgg acttgccttt ccttctcttc    180

tccgcgtgtg gagggagcca gcgcttaggc cggagcgagc ctgggggccg cccgccgtga    240

agacatcgcg gggaccgatt cacc atg gag ggc gcc ggc ggc gcg aac gac      291
                           Met Glu Gly Ala Gly Gly Ala Asn Asp
                             1               5

aag aaa aag ata agt tct gaa cgt cga aaa gaa aag tct cga gat gca      339
Lys Lys Lys Ile Ser Ser Glu Arg Arg Lys Glu Lys Ser Arg Asp Ala
 10                  15                  20                  25

gcc aga tct cgg cga agt aaa gaa tct gaa gtt ttt tat gag ctt gct      387
Ala Arg Ser Arg Arg Ser Lys Glu Ser Glu Val Phe Tyr Glu Leu Ala
                 30                  35                  40

cat cag ttg cca ctt cca cat aat gtg agt tcg cat ctt gat aag gcc      435
His Gln Leu Pro Leu Pro His Asn Val Ser Ser His Leu Asp Lys Ala
             45                  50                  55

tct gtg atg agg ctt acc atc agc tat ttg cgt gtg agg aaa ctt ctg      483
Ser Val Met Arg Leu Thr Ile Ser Tyr Leu Arg Val Arg Lys Leu Leu
         60                  65                  70

gat gct ggt gat ttg gat att gaa gat gac atg aaa gca cag atg aat      531
Asp Ala Gly Asp Leu Asp Ile Glu Asp Asp Met Lys Ala Gln Met Asn
     75                  80                  85

tgc ttt tat ttg aaa gcc ttg gat ggt ttt gtt atg gtt ctc aca gat      579
Cys Phe Tyr Leu Lys Ala Leu Asp Gly Phe Val Met Val Leu Thr Asp
 90                  95                 100                 105
```

-continued

```
gat ggt gac atg att tac att tct gat aat gtg aac aaa tac atg gga      627
Asp Gly Asp Met Ile Tyr Ile Ser Asp Asn Val Asn Lys Tyr Met Gly
                110                 115                 120

tta act cag ttt gaa cta act gga cac agt gtg ttt gat ttt act cat      675
Leu Thr Gln Phe Glu Leu Thr Gly His Ser Val Phe Asp Phe Thr His
            125                 130                 135

cca tgt gac cat gag gaa atg aga gaa atg ctt aca cac aga aat ggc      723
Pro Cys Asp His Glu Glu Met Arg Glu Met Leu Thr His Arg Asn Gly
        140                 145                 150

ctt gtg aaa aag ggt aaa gaa caa aac aca cag cga agc ttt ttt ctc      771
Leu Val Lys Lys Gly Lys Glu Gln Asn Thr Gln Arg Ser Phe Phe Leu
    155                 160                 165

aga atg aag tgt acc cta act agc cga gga aga act atg aac ata aag      819
Arg Met Lys Cys Thr Leu Thr Ser Arg Gly Arg Thr Met Asn Ile Lys
170                 175                 180                 185

tct gca aca tgg aag gta ttg cac tgc aca ggc cac att cac gta tat      867
Ser Ala Thr Trp Lys Val Leu His Cys Thr Gly His Ile His Val Tyr
                190                 195                 200

gat acc aac agt aac caa cct cag tgt ggg tat aag aaa cca cct atg      915
Asp Thr Asn Ser Asn Gln Pro Gln Cys Gly Tyr Lys Lys Pro Pro Met
            205                 210                 215

acc tgc ttg gtg ctg att tgt gaa ccc att cct cac cca tca aat att      963
Thr Cys Leu Val Leu Ile Cys Glu Pro Ile Pro His Pro Ser Asn Ile
        220                 225                 230

gaa att cct tta gat agc aag act ttc ctc agt cga cac agc ctg gat     1011
Glu Ile Pro Leu Asp Ser Lys Thr Phe Leu Ser Arg His Ser Leu Asp
    235                 240                 245

atg aaa ttt tct tat tgt gat gaa aga att acc gaa ttg atg gga tat     1059
Met Lys Phe Ser Tyr Cys Asp Glu Arg Ile Thr Glu Leu Met Gly Tyr
250                 255                 260                 265

gag cca gaa gaa ctt tta ggc cgc tca att tat gaa tat tat cat gct     1107
Glu Pro Glu Glu Leu Leu Gly Arg Ser Ile Tyr Glu Tyr Tyr His Ala
                270                 275                 280

ttg gac tct gat cat ctg acc aaa act cat cat gat atg ttt act aaa     1155
Leu Asp Ser Asp His Leu Thr Lys Thr His His Asp Met Phe Thr Lys
            285                 290                 295

gga caa gtc acc aca gga cag tac agg atg ctt gcc aaa aga ggt gga     1203
Gly Gln Val Thr Thr Gly Gln Tyr Arg Met Leu Ala Lys Arg Gly Gly
        300                 305                 310

tat gtc tgg gtt gaa act caa gca act gtc ata tat aac acc aag aat     1251
Tyr Val Trp Val Glu Thr Gln Ala Thr Val Ile Tyr Asn Thr Lys Asn
    315                 320                 325

tct caa cca cag tgc att gta tgt gtg aat tac gtt gtg agt ggt att     1299
Ser Gln Pro Gln Cys Ile Val Cys Val Asn Tyr Val Val Ser Gly Ile
330                 335                 340                 345

att cag cac gac ttg att ttc tcc ctt caa caa aca gaa tgt gtc ctt     1347
Ile Gln His Asp Leu Ile Phe Ser Leu Gln Gln Thr Glu Cys Val Leu
                350                 355                 360

aaa ccg gtt gaa tct tca gat atg aaa atg act cag cta ttc acc aaa     1395
Lys Pro Val Glu Ser Ser Asp Met Lys Met Thr Gln Leu Phe Thr Lys
            365                 370                 375

gtt gaa tca gaa gat aca agt agc ctc ttt gac aaa ctt aag aag gaa     1443
Val Glu Ser Glu Asp Thr Ser Ser Leu Phe Asp Lys Leu Lys Lys Glu
        380                 385                 390

cct gat gct tta act ttg ctg gcc cca gcc gct gga gac aca atc ata     1491
Pro Asp Ala Leu Thr Leu Leu Ala Pro Ala Ala Gly Asp Thr Ile Ile
    395                 400                 405

tct tta gat ttt ggc agc aac gac aca gaa act gat gac cag caa ctt     1539
Ser Leu Asp Phe Gly Ser Asn Asp Thr Glu Thr Asp Asp Gln Gln Leu
410                 415                 420                 425
```

-continued

```
gag gaa gta cca tta tat aat gat gta atg ctc ccc tca ccc aac gaa     1587
Glu Glu Val Pro Leu Tyr Asn Asp Val Met Leu Pro Ser Pro Asn Glu
                430                 435                 440

aaa tta cag aat ata aat ttg gca atg tct cca tta ccc acc gct gaa     1635
Lys Leu Gln Asn Ile Asn Leu Ala Met Ser Pro Leu Pro Thr Ala Glu
            445                 450                 455

acg cca aag cca ctt cga agt agt gct gac cct gca ctc aat caa gaa     1683
Thr Pro Lys Pro Leu Arg Ser Ser Ala Asp Pro Ala Leu Asn Gln Glu
        460                 465                 470

gtt gca tta aaa tta gaa cca aat cca gag tca ctg gaa ctt tct ttt     1731
Val Ala Leu Lys Leu Glu Pro Asn Pro Glu Ser Leu Glu Leu Ser Phe
    475                 480                 485

acc atg ccc cag att cag gat cag aca cct agt cct tcc gat gga agc     1779
Thr Met Pro Gln Ile Gln Asp Gln Thr Pro Ser Pro Ser Asp Gly Ser
490                 495                 500                 505

act aga caa agt tca cct gag cct aat agt ccc agt gaa tat tgt ttt     1827
Thr Arg Gln Ser Ser Pro Glu Pro Asn Ser Pro Ser Glu Tyr Cys Phe
                510                 515                 520

tat gtg gat agt gat atg gtc aat gaa ttc aag ttg gaa ttg gta gaa     1875
Tyr Val Asp Ser Asp Met Val Asn Glu Phe Lys Leu Glu Leu Val Glu
            525                 530                 535

aaa ctt ttt gct gaa gac aca gaa gca aag aac cca ttt tct act cag     1923
Lys Leu Phe Ala Glu Asp Thr Glu Ala Lys Asn Pro Phe Ser Thr Gln
        540                 545                 550

gac aca gat tta gac ttg gag atg tta gct ccc tat atc cca atg gat     1971
Asp Thr Asp Leu Asp Leu Glu Met Leu Ala Pro Tyr Ile Pro Met Asp
    555                 560                 565

gat gac ttc cag tta cgt tcc ttc gat cag ttg tca cca tta gaa agc     2019
Asp Asp Phe Gln Leu Arg Ser Phe Asp Gln Leu Ser Pro Leu Glu Ser
570                 575                 580                 585

agt tcc gca agc cct gaa agc gca agt cct caa agc aca gtt aca gta     2067
Ser Ser Ala Ser Pro Glu Ser Ala Ser Pro Gln Ser Thr Val Thr Val
                590                 595                 600

ttc cag cag act caa ata caa gaa cct act gct aat gcc acc act acc     2115
Phe Gln Gln Thr Gln Ile Gln Glu Pro Thr Ala Asn Ala Thr Thr Thr
            605                 610                 615

act gcc acc act gat gaa tta aaa aca gtg aca aaa gac cgt atg gaa     2163
Thr Ala Thr Thr Asp Glu Leu Lys Thr Val Thr Lys Asp Arg Met Glu
        620                 625                 630

gac att aaa ata ttg att gca tct cca tct cct acc cac ata cat aaa     2211
Asp Ile Lys Ile Leu Ile Ala Ser Pro Ser Pro Thr His Ile His Lys
    635                 640                 645

gaa act act agt gcc aca tca tca cca tat aga gat act caa agt cgg     2259
Glu Thr Thr Ser Ala Thr Ser Ser Pro Tyr Arg Asp Thr Gln Ser Arg
650                 655                 660                 665

aca gcc tca cca aac aga gca gga aaa gga gtc ata gaa cag aca gaa     2307
Thr Ala Ser Pro Asn Arg Ala Gly Lys Gly Val Ile Glu Gln Thr Glu
                670                 675                 680

aaa tct cat cca aga agc cct aac gtg tta tct gtc gct ttg agt caa     2355
Lys Ser His Pro Arg Ser Pro Asn Val Leu Ser Val Ala Leu Ser Gln
            685                 690                 695

aga act aca gtt cct gag gaa gaa cta aat cca aag ata cta gct ttg     2403
Arg Thr Thr Val Pro Glu Glu Glu Leu Asn Pro Lys Ile Leu Ala Leu
        700                 705                 710

cag aat gct cag aga aag cga aaa atg gaa cat gat ggt tca ctt ttt     2451
Gln Asn Ala Gln Arg Lys Arg Lys Met Glu His Asp Gly Ser Leu Phe
    715                 720                 725

caa gca gta gga att gga aca tta tta cag cag cca gac gat cat gca     2499
Gln Ala Val Gly Ile Gly Thr Leu Leu Gln Gln Pro Asp Asp His Ala
```

-continued

```
730                 735                 740                 745

gct act aca tca ctt tct tgg aaa cgt gta aaa gga tgc aaa tct agt      2547
Ala Thr Thr Ser Leu Ser Trp Lys Arg Val Lys Gly Cys Lys Ser Ser
            750                 755                 760

gaa cag aat gga atg gag caa aag aca att att tta ata ccc tct gat      2595
Glu Gln Asn Gly Met Glu Gln Lys Thr Ile Ile Leu Ile Pro Ser Asp
            765                 770                 775

tta gca tgt aga ctg ctg ggg caa tca atg gat gaa agt gga tta cca      2643
Leu Ala Cys Arg Leu Leu Gly Gln Ser Met Asp Glu Ser Gly Leu Pro
        780                 785                 790

cag ctg acc agt tat gat tgt gaa gtt aat gct cct ata caa ggc agc      2691
Gln Leu Thr Ser Tyr Asp Cys Glu Val Asn Ala Pro Ile Gln Gly Ser
    795                 800                 805

aga aac cta ctg cag ggt gaa gaa tta ctc aga gct ttg gat caa gtt      2739
Arg Asn Leu Leu Gln Gly Glu Glu Leu Leu Arg Ala Leu Asp Gln Val
810                 815                 820                 825

aac tga gctttttctt aatttcattc ctttttttgg acactggtgg ctcactacct      2795
Asn

aaagcagtct atttatattt tctacatcta attttagaag cctggctaca atactgcaca    2855

aacttggtta gttcaatttt tgatcccctt tctacttaat ttacattaat gctctttttt    2915

agtatgttct ttaatgctgg atcacagaca gctcattttc tcagtttttt ggtatttaaa    2975

ccattgcatt gcagtagcat cattttaaaa aatgcacctt tttatttatt tatttttggc    3035

tagggagttt atccctttt cgaattattt ttaagaagat gccaatataa tttttgtaag     3095

aaggcagtaa cctttcatca tgatcatagg cagttgaaaa atttttacac cttttttttc    3155

acattttaca taaataataa tgctttgcca gcagtacgtg gtagccacaa ttgcacaata    3215

tattttctta aaaaatacca gcagttactc atggaatata ttctgcgttt ataaaactag    3275

tttttaagaa gaaatttttt ttggcctatg aaattgttaa acctggaaca tgacattgtt    3335

aatcatataa taatgattct taaatgctgt atggtttatt atttaaatgg gtaaagccat    3395

ttacataata tagaaagata tgcatatatc tagaaggtat gtggcattta tttggataaa    3455

attctcaatt cagagaaatc atctgatgtt tctatagtca ctttgccagc tcaaaagaaa    3515

acaataccct atgtagttgt ggaagtttat gctaatattg tgtaactgat attaaaccta    3575

aatgttctgc ctaccctgtt ggtataaaga tattttgagc agactgtaaa caagaaaaaa    3635

aaaatcatgc attcttagca aaattgccta gtatgttaat ttgctcaaaa tacaatgttt    3695

gattttatgc actttgtcgc tattaacatc cttttttca tgtagatttc aataattgag     3755

taattttaga agcattattt taggaatata tagttgtcac agtaaatatc ttgtttttc     3815

tatgtacatt gtacaaattt ttcattcctt ttgctctttg tggttggatc taacactaac    3875

tgtattgttt tgttacatca aataaacatc ttctgtggaa aaaaaaaaaa aaaaaaa       3933
```

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5

```
ccagttacgt tccttcgatc agt                                              23
```

<210> SEQ ID NO 6
<211> LENGTH: 20
<212> TYPE: DNA

-continued

<213> ORGANISM: Artificial Sequence
<220> FEATURE:
<223> OTHER INFORMATION: PCR Primer

<400> SEQUENCE: 6
tttgaggact tgcgctttca 20

<210> SEQ ID NO 7
<211> LENGTH: 28
<212> TYPE: DNA
<213> ORGANISM: Artificial Sequence
<220> FEATURE:
<223> OTHER INFORMATION: PCR Probe

<400> SEQUENCE: 7
tcaccattag aaagcagttc cgcaagcc 28

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc 19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc 20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc 20

<210> SEQ ID NO 11
<211> LENGTH: 57501
<212> TYPE: DNA
<213> ORGANISM: H. sapiens

<400> SEQUENCE: 11
ttaaaatttt atcctatatg aaattttcct ttttggtgtc tgttatttaa taggattgtt 60
tgaattaggg gatactattt ggtgcctttg taactatatg aaaattagtt ggttgaatat 120
tactgctttc catgttcata tttatatttg tatagacata tatatatata cacatatact 180
actttccttt ccattttcat atttatattt gtgtatacac atatacataa acatatattt 240
tatacatttt tgaaaaggaa aattaactta agggcatatt taatgaatat tcaaaaattt 300
ttttgctgat caaattatca ttctgcttta aacttttgaa atgatccaaa aaaattttaa 360
atgacttaga tttactgtta caaaatgctt gtcttttgat gtcacaaaca ttatatacta 420
taatcactgg ccagagataa ttgctataag tataatgaaa agggaaatga tggaagatct 480

```
ctgcagctat cctcataaat gagggtggga acacgatggg cagttccaaa gttgaaaata    540
gagaatatat gtggatttat attaacataa ttggtattct tggatagtta aaaatggcta    600
aactgtagga gaagcccgag taattactgt taacagagga ataaatttga gggcaataat    660
aatgatgata ggccaggcac tgtggctcat gcctgtaatc ccagcacttt gggaacccga    720
ggcgagcgga ccacctgagg tcaggagttc gagagcagcc tggccaacat ggtgaaacct    780
cgtctctact aaaaatagaa aaattatccg agtgtggtgg tgcgtgcctg taatcccagc    840
tacttgggag gctgaggcag gagaatcact tgtacctggg aggcggagtt gcagtgagcc    900
gaaatcgcgc cactgcgctc cagcctgtgg gccagagcga gactccgcct cagaataata    960
ataatgataa taataataac gccaccaaca atactaagag ctaacattta ctgagtgctt   1020
actatgcacc agatattgtt ctaagtatac atttattatc tcatttaacc atccataata   1080
ctgtggtata gacactttta tatccatttt ataaataagt aaactgagtt atggagagat   1140
taaacgactt gccagtaaga ttcaaagcct gtgtacaagc tcacgcttga ttctggagcc   1200
agtgttctta acacagtatc ttgagaatgt taaactaaaa agtttttaat ttacagtatt   1260
ctttccacaa ttaaaaaaga aattatgagt aattattttt agttctttct tctcttcagg   1320
catttcccat ggttcttttc aagacataat acatatcatt tagtgttgta gatctgaaaa   1380
aacaaaagta gcgtgaagat caaaaatttt ctaaagagac ggagtctcgc tacgttccct   1440
aggctggaac acccaggctt ctccagcctc acacctctga gtagctggaa ccaccctgtc   1500
cgctaaggtc aatgtttaat cgtatctttg taggtctact gaccagttaa aaagaggtgc   1560
tgtatacatt ggttgttgtc ttgtcagagt ttgatgcttc tatatagacc attgttttta   1620
catgctaata caattgaaag ccactacaga tatttatatt tacaacccaa agctaggttt   1680
taacaagaaa ctcataaggc aaaggtgaga agtaaaataa tttagcgcca agtggagata   1740
tatgtgcaat gctactttgt tgggctcaaa acatattttt cttttagaag actgacaggc   1800
ttgaagttta tgcctccaaa gacaaaagtg attatgtttt gtttagtagc ttgcaaagtt   1860
gccaaaggcc atttttctta ctctttccct gaaattggtt tatatgctta ttaaagtcat   1920
ttatacctat ttgcaaatgc ttaacatagt ttcagatttt aagatttccc tgcaacttta   1980
tttcccttga agtttacagc aacaggagtt catttttatt tttaattgca tttattcagt   2040
aagtaaactc cgccacagaa aaacttagta gacaaggtga gttcccctgt gctccgtggc   2100
aaagagtgcg gtgggtgaca ttgacccatg gttaggtaat ctggtaagga aagaccccgt   2160
tgtaacacat ctgagcaacg agaccaaagg aagggcttgc tgccacgagg cgaagtctgc   2220
ttttttgaac agagagccca gcagagttgg gcggcaatcg tgcccagcac tgaggccgag   2280
gagaaagaga gcaggagcat tacattactg caccaagagt aggaaaatat gatgcatgtt   2340
tgggaccagg caaccgaaat cccttctcag cagcgcctcc caaagccggg caccgccttc   2400
cttcggagaa ggcgcagagt ccccagactc gggctgagcc gcacccccat ctcctttctc   2460
tttcctccgc cgctaaacac agacgagcac gtgagcgtcg cagcccgtcc cagctgtgcc   2520
tcagctgacc gcctcctgat tggctgagag cggcgtgggc tggggtgggg acttgccgcc   2580
tgcgtcgctc gccattggat ctcgaggaac ccgcctccac ctcaggtgag gcgggcttgc   2640
gggagcgcgc gccggcctgg gcaggcgagc gggcgcgctc ccgccccctc tcccctcccc   2700
gcgcgcccga gcgcgcctcc gcccttgccc gccccctgac gctgcctcag ctcctcagtg   2760
cacagtgctg cctcgtctga ggggacagga ggatcaccct cttcgtcgct tcggccagtg   2820
```

-continued

```
tgtcgggctg ggccctgaca agccacctga ggagaggctc ggagccgggc ccggaccccg   2880
gcgattgccg cccgcttctc tctagtctca cgaggggttt cccgcctcgc acccccacct   2940
ctggacttgc ctttccttct cttctccgcg tgtggaggga gccagcgctt aggccggagc   3000
gagcctgggg gccgcccgcc gtgaagacat cgcggggacc gattcaccat ggagggcgcc   3060
ggcggcgcga acgacaagaa aaagtaagcc cattccctcg gcccgccgcc ttctcccccg   3120
gcgaccccgc ccgcctgccc gccctgggct cctgggccgg cctcggcgtt aatgggattg   3180
gggggggcag cctttttgtt tctgctgctg ctcccctccc ctctcttccc ccaacctcgc   3240
cggccgggct cccccgctgt ccacgtcgcc atcttgtcgt ggggggtggg agacgcctcg   3300
aaagtgcttt caggggccgg ggtctgagcc ctgcttgccc tccccgccgg ccgtgggggc   3360
ctcgcgccgc ccacctaccc gcctcaaaaa cccagcctgc tctgtggccc catccggagg   3420
ggactttacc cagcctgaaa accccgggaa gagaaatgag ctgcagctcg gtagccgcgg   3480
tttgcacccg gagcttccgc tccttcccgc ccccatcctc tccagttcca ttgaaaactc   3540
ggccctgggg cggaccctgc acgctggtcc tggctttcca gtggacttgg ggccttgagt   3600
tcccgactga gggactcgcg tggtcggatg cgatcttgtc ctgtagttgt ccagccgtcg   3660
cgggtgtctt tgcctttgtg cattagggat ttgccgcgat ggccttaaga tgcgaacttt   3720
ttagtttgca cgtgcaggtt ttgtttcgtt ttaatcgcct tgaaaaactt gcctagactg   3780
agagtcagag taatgggaat ttagggaaat ggcaacattt taaagagaac ttcagaattg   3840
gatacttgag ttcatatcac ctgtcacgag aacgcagata ttataaatga atatatgcct   3900
cattcattct tcaaataatg aaaatgtagg ggctggttaa atttaggcag ttttaatgat   3960
actgaaaaaa gtatatgatg agtgaatgaa atgcggcact aaaatgttgc aaaaattttc   4020
gaactctgtc tcattttcct gaaattgaag tatattaaag gaaaaccgtc aacatatatc   4080
taaagtaagt aatcactcgg ttagaactta atgcaagttt tataaatcac cttgaagttt   4140
gagtctaagg ggtacattag agattaagaa ttgtgagttg gaccagtggt gttaagagcg   4200
gactccccca tcccccaaca cacacacaat tttgcccact ttggcatttt aacttttaag   4260
gaaatcactt aaggaattga agatttagag taagagtttt ggttagtaga ctggctttgc   4320
tgttaaatcc ttccactctt ctggcagaga gattaatttc cctaatcagt atcagcagaa   4380
gataaacttg tttatattcc tgctgttttg tagatccctt ctcctggtcc ttcttcaata   4440
gaatattaaa ttcttagttt gtatacagca gagaaggtca cttataaaat tcaaaaagtg   4500
agcaaacagg tctagattaa ttccaagagt taccaggaat taattgcagt ttattttgcg   4560
gaggtgatta cagtgctttt gatgaaatga taaagctgct atattgtaaa cctaaggcag   4620
attacctctg tgtagtgcca gttttctatc cttattatat attgaatcat acttaataca   4680
atgcattaaa ttatgtacca ctttttttat atacagtatc gaactcattg ttttgccatt   4740
catccgttca gaatatcaga agcagttttg aaacgaatta ataaattagc tactgttcat   4800
cagccccaat tctaaataag ctcttagatt ttcctcagcc catctgttac tttcaaaatt   4860
ttctcatttg aaaacttggc aaccttggat tggatggatt catatttctt agtatagaag   4920
ttcttgatat aactgaaaaa ttaagttaaa cacttaataa gtggtggtta ctcagcactt   4980
ttagatgctg tttataatag atgacctttt ctaactaatt tacagttttt tgaaagataa   5040
ctgagaggtt gagggacgga gattttcttc aagcaatttt ttttttcatt ttaaatgagc   5100
tcccaatgtc ggagtttgga aaacaaattt gtctttttaa aagaaggtct aggaaactca   5160
aaacctgaag aattggaaga aatcagaata gaaaatgggt atggttatga tactgtagat   5220
```

-continued

```
ttaacgcagg acatttcatg ttgttcctag ttataggggc tgaacttatt taatagcacg   5280
tgcattttga tttttagatt tttaagggaa tgtcaagaga gtaatgattc tgtttcaggc   5340
ttcaggccag actccttcag agttttccaa aacaaataat tactgaatca ttaaagtaaa   5400
atttctgaga atagatattc cttaatttcc ttcattaact ttggccatta aaagtcaaga   5460
agctctctca tttattagca aacttttctc cttatgattc tattttgatt gtccttttgt   5520
ttgaggaagc agcatatggt ggttaagagc ataggatcta gaggcagata cctctgagtt   5580
aagggtccca gcccttcact tgtgagcttg agcaagttac tgaatgcctc tgagcctctt   5640
tcctcctttt gaaatgatga taagaatagc agccatctga gcagttattg taaaggttaa   5700
atgagataat gcttgtgaag cacttagccc attgcaggag tcttgatgac actgtgtact   5760
tgaaaataga tgttacctgt taaaattctt gtttaaactt ccacaactct taaaactctt   5820
ttttgctagt ccttccagct gtttccttta gtttcttttc tgtgtcttca tgcatctttt   5880
ctatctcctg aaagtgaaaa gactaacatt ggatccagag cttgaaaagc gtttttttcc   5940
tgttacaatg ggcaaaagag tacatccttg ggttatattg gcacctagta tcagttattt   6000
ttcttgagca tctgatctgc tctctactct agtggaggcc tcctgcttca caattgctca   6060
cccctgtgtt ttctccccaa atagaatact gagtttactc tggactctag agtcaaacat   6120
acacagtatt ctagtcttac tgttcattta agcaagatat gtgcaagaca ctgcattctt   6180
agtactggca gtaagttaaa acatttttcg tcttgatgcc aaagtttaga caattttata   6240
aaaattaacc tttgtaaaag ataatgagtt gataaaatat tctcagtaaa gcagctacgt   6300
ggtagaaaaa ctgtcctttg cttatgagtt tctccagagt taagaccatt gggttccatc   6360
tgaaggcaag acttcaagct tgtcttactg gtctgttttg tggctcaatt tgtatgaagt   6420
ctatgcactc ttccacacgt gtgtatttac tgaactatcg agttatttta gactgagaaa   6480
gtattggagt tcattcctac ggtccactgc agagcacctt gtgcagtttg gagaatgtca   6540
acttttctac ctgttaactt ccattgtctt tacttttaac gccattgtct gtgactctaa   6600
tggtgtcacg gctcagggtt tagattttgt ggttacattc tattcttgta tgtcaagagt   6660
ggtgtataga aagctgaggg ggattattta gtctcttgac tgattttttt ttttttttctg  6720
aagaactcag tttattatgt ttggtggtga aataaaaatt gatgtgcatg gatgttaaag   6780
atttgggtta aattgtgtgt tcatagatgc cttctcttag tatataattt tttaaattta   6840
gatacttaaa atactgtatc cctttatcta agattaacat aagtctgttt cttaaccagg   6900
ataaaaaaat ctaaatttaa atgtgatgtt ggatgagttt ccaatcaaga aattgatttt   6960
ttaaactttg tgactagtta tccagtgggt ggattttacc cagtgtgtgt atgtgttttc   7020
tgcttaactc tggaaggtta gaaagagaat ttgaaactaa gacaagccaa gcttcttgtt   7080
gctcagtatt tttggtaaaa atatggtcag attgtttaaa ttaactatag gctttggaat   7140
tttaaaaata attatatctc ttggtctctt gacacatcaa gaattaactg ttttgtatat   7200
gcgttgagta ttaatgttca tgttttctgc agtagaaatt tataaaccct tatttatttg   7260
ccagacatga tccctttaga gaaatctagt atctaaaacc tgaattttta aaacaaaatt   7320
taaaattttt gtttcataaa aacaaaaatg tgattacctc atggcttttt tcttatagct   7380
tttgattgtt ttttaaaatc gtagttcaaa aacattaacc taaaatttac catcttaacc   7440
atttctaagt actgttcagt agtgttaagt atattcacat tgtgccacta acttccagaa   7500
ctttttcatc ttgcaaagct gaaatcttac ccattaaaca actcccaatt tccccctctc   7560
```

-continued

```
ctcagcctct ggcaaccacc attttacttt ctgtttctgc aaatttaact actctagatg   7620
cctcatataa atagaattat aggttttaa tatttttgtg atgggcttat ttcactttgt   7680
gtaatgtcct caaggttcat ccatgttgta gcatgtgtca gaatttcctt cctttttgag   7740
tctgagcaat attccattat atgttccata ttttgtttct ccattcatcc agcaacggac   7800
acttgggttg cttccacatc ttggttattg tgctgctctg aacatgagtc tgcaaatctc   7860
tctttgaagc tttcactttt tttggataca tatccagaag agggatgctg gatcatatgg   7920
taacccttt taattttcaa ggaaccacca tattgttttc tatagcagtt gcaccagttt   7980
acattcccac caacagtgca caagggttcc tatttctcca catccttcta aacacttgtt   8040
ttctttcttt ccttccttct cttctctttc tttcttagcc atctaatgtg gcaaagtggt   8100
agccatctaa tatgttgaag tgattgtttt taagggcttg tttgtggata attaaccagc   8160
tgaaagctaa ctacagtttg ccagtggaag ctttaactga aaggagagta agtacctcta   8220
aaaggagaat tcaattttc tagtgactta gatttgttat gccagtactt tttcacagaa   8280
acacttttg ggtaaaatag tgtacacctg ttctattgtt gataaagccc aatttaatta   8340
ggaaatttgt tctctaagat ttaaaacaat aattgaaata atgtattttt attaaaaact   8400
gttcccaaga tgttagcttt tagctgttct ggtgatctca actgttattt atgagtgttt   8460
ctttatttta aaatttcacc ttaaccggtt acagttttaa ccataaagat tatttcaaca   8520
tatgattttg aaaatttatt atcttgtaaa tgggaaaatg tagtgatgga acatagttta   8580
ctgtatgtag ttcttcactt gtttgaaaag tcacaatata tttaggcaaa ttaatttaaa   8640
agtgtctagt atttaatatt gcaattttca ctcattaagg acaggtcccc cgtgtttccc   8700
cctttttttt ttccaagtag tttgggagga tttgtttttc cagctgaaaa atactatggt   8760
taaaaataag gtttaaaggc gaaagttgaa gtctttgagg gttgggatac gtttctgttc   8820
ttaagagtct tgtaaattca gatgctaagc aaatttcttt aaaatgattt ctaccctccc   8880
cctttccatt ataaaactgg atatgtttca gtggaccaaa tcccaagtag gctgaatttg   8940
aaatttgtgg gctgggcgcg gtggctcatg cttgtaatcc cagtactttg ggatgccgag   9000
gtgggtggat cacctgaggt caggagttcg agaccagcct ggccaacatg gtgaaacccc   9060
atctctacta aaaataccaa aattagccag gcgtggtggc gggtgcctgt aatcccagct   9120
acttaggagg ctgaggcagg agaattgctt gaacctggga ggcggaggtt gcggtgagcc   9180
aagatcgccc cattgcactc cagcctgggt gacagagcaa gactgtgttt caaaaaaatt   9240
aaaaaagaaa tctgtggtgt gaatactggt acgtggtgta cacagtgagc tcttaataag   9300
tatttgaatt aacaaatgag acaatgattg aataattgga tgaacaaaga gaatgcaggt   9360
ttttaaaagg tttctttaga aatattgtcg gcccggcacg gtggctcctg cctgtaatcc   9420
caccattttg ggaggccggg gcaggtgaat cacctgaggt caggagttca agacaagcct   9480
gaccaacttg gagaaacccc gtctctacta aaaatacaaa aaaaaaaaaa aaaaaatagc   9540
aggatgtggt ggcacatgcc tgtaatccca gctactcgga ggctgaggca ggagaatcgc   9600
ttgaacctgg gaagcagagg ttgcagtgag ccaagatcgc gccactgcac tccagcctga   9660
tgacagtgtg agatgctgtc tccaaaaaaa aaaaaaaaaa attaaaaaga atgttttaat   9720
tctttagttc cctgtctgag attcactgat tggtaagaag aaagttaaag aatctccttt   9780
gactttttt gatatagata tttaaattct attactttat agtaaggttg gggtttattt   9840
tctttgcttt ataatagaag agcattgatt attctctttg ctttataata gaataccatt   9900
taaataggag ttccctgagt gtgtttacaa tcatttgatc tggctaaact attttaatgt   9960
```

-continued

```
taatgaaatt ttaaaatttt ggaggaaaaa atttaaaaac tacacaggtg cacaaagaaa  10020
taaaaatcac ctgctttttc actatgtaga gaccattgtc tactatttct caattctgtg  10080
ttacatctgt atgttaataa ctgtaggatt agggactgag tactgttttt aacctgcttt  10140
taaaaaattt acatctacat tttttcccat ctaaatagtg aggaagagta tcagaatttt  10200
gtaggcttgt ggtgatggtt aaattagata atattaatgt tgggtactta acataatata  10260
tggctcttaa tactctccag atttcagata tagtctgttt taccattact gccttttttat  10320
caaacctatt ctcaaaaaag tgagaaaagt gctgagatta caggcgtgag ccaccatgcc  10380
cggcctcatg gttctttctt aataataaat tagaagaagt agaattacag ggtcaaaaag  10440
tatccatttt aaagctttca atgtaattgc ctgtttatct tctagaaagt ttgacctagt  10500
tgtattttag agtgtcattt tcttgaactt tatcatcatt aaagttttaa atttggaaca  10560
ctggcaattt gataagtata ttaggattct tcttattgca agtagcaaaa tacaactcaa  10620
tctagtttaa gaggggaaaa tgtagtcatt ggctaacaca atctaatttt ggtttaagag  10680
acaaatctag agtctcaaat gatctcagag tgtaataatc cctgactttt gtcttgatat  10740
tacttggctt gtataccttt gctctatttg catgctggcc ttactctgcc actgacaggc  10800
tgtctgtatg gtgtggaaga ggacggctag catccccata cctgcatcca tacagtttgt  10860
aatataaaaa aaaaaaaagt aaaaaaaact ccctctctct tctagtgtct atatatcagt  10920
ttcctagaag aaaacgtttt gccctacttg gccatgtgaa tggagttccc tgattacatg  10980
agtcaaatat gtcttattgt agcatatttg atggtcttct tgtagaatat tatcttacta  11040
tacacagaac tcttgaccag taattaatgg gccatgagtt tttgttgcaa gtcatttgaa  11100
ttcatattct atagttttct accaagtgta gtcattctgc aagctgttct tgtcatgact  11160
tttgggaagt tgagtatttc ttctatgggt tagggttttc atctcaagaa aaagatgatc  11220
cttttctcta ctaaatatgt gttaagatca cacatttttc tagatcgttt agctctactg  11280
tgtgatctta cacaaattgc tttattggga tgataagaat aattgcctta taggattgtt  11340
atgagaatga aatgatacat caactcatat gaaacactca gaacagctct tggcacaaag  11400
taagggctta attaagtaga aactatccat atattcataa tattatagta ttggttaagt  11460
tgttttcaac attgtttaga atcgctcaag ccttctttgt gataatctga cgaaggctat  11520
tcaccaccag tgagtaaata atagtggcag aatagttact gatgcttttc ctttacttgg  11580
tttttttcc ataaacatct ggcctttgca gactaaatac tggtttatgt atagacatgt  11640
tattctaaaa taattttcca tagtggtaat actaaaggaa gaaaaatgtt ctcaaagcta  11700
tttatttggg atgttaaagg agggggaaat taagaaagcc tacatttcca tgtcctttgt  11760
gtccagaatc tcattaaatg tcttttaact tgttagcaga ggaaagttgg atattgcctg  11820
cctttgtagc taacatagtt aaaatattta aatggttata gtgtcaaacc agtagtcaaa  11880
gccttcactg tgaatggatg aagggatatt ttcttgaata atttaagttg acttatttca  11940
gtggttcaaa aaatttcttc aacgcttaac catgactcag gcacctaact attatactat  12000
gtcctgtaac agattgttgt gcattcattt attcaacagg tatttgtgca gctaatttat  12060
tgagtacagc attgaatcgt tgatggctta ggccacagtt gaacattcca ttttttatgt  12120
tcattcattc attcatagca tattccattt ttaaattttc agttcattgc actttaaagt  12180
ttgaggttct tgcgaagtac agacttttgg gtttaagttt tgttatttaa tgtcaaccac  12240
cacaggcgca ttggccagtc tgcttttaga attttcagac atacatacac aaaacattct  12300
```

-continued

```
cacaagacaa tctacttatt ttcttttttta ttcctgtgtt tcttaacaca ggattaatgt  12360
tcagatctct tttggagcaa aataatcctc tgaatttttg agatgtaccc agtgacctca  12420
gtctgagtat gtatactgca ttaaaaaatg taaccttgtt ccttttagtg gtcatttggt  12480
aacagtttga tcataaacaa atgcagcctc aaacacagaa ggcttgaggc aagtatacag  12540
aactatggag agatcattta gatgatgtag aatatgcctt ttcttttttt acaatgccac  12600
caaaatgaaa acacggtttt aaaaattctc atagagtgta acttcaacac tgctttaact  12660
ctattaaaca aagcactgcc atgttgtaat tcctatttat tactctctgg agttgtataa  12720
attaccaaat ccgccttttg tttgatatcc ttttcaaata tctgagggta gctatcatgt  12780
ttcttccttc tattcttaaa aaatagtccc aaatttcttg aatcttttaa tttaaaaatt  12840
atatattgag catctgattt gtggaaaggc ataggccata ttaaaaatgg ggcttcatat  12900
taaaatgggg aaaagggtgg agattctcag gtggaatctg agatctgcca cacactaata  12960
gtgttaccta accctttttta aagacaaaga aacaggatca gaaggtcact ttggaaaatt  13020
tatttggtaa tattggatag gatggattag tatagttgga aaacagagac tcttgcttta  13080
ggagagctgc tcctttgtca tttccagaat cttaatcatg gtcaaggttt agagctaaat  13140
atttaataga agaagtcttt agggtatgct ttctattgta cacccttatt tcaatacatg  13200
tgttttttcc tgttatgtaa gtactttatt attatttatg catcttctat taaagttaag  13260
caaataatta tttcaaggac acattcttct acatacacac aaagtttagg gtcactgacc  13320
ttcttaggtt ctagtcttag atctgttacc atctaagagc atataaataa gggaaacaga  13380
aagaaaagga tttacaagct gagaaggaag caatgcagag aaagaagagt gatagagtag  13440
gtaatttggg gaaagtcagt gatacacagc tcttaaccat gaacagtgat tcttcactct  13500
tgaatgtttg tgacattcat gaaggtatta aaagctgact tttaaaaaat tgtttcagag  13560
aactggaaaa aaattcagtt gccacattct tccttaggtc atctttgaac tctactcatg  13620
cacttacgtg tttaaggcaa agttttacta aacgcacact tgttcttgct ggcttattga  13680
cttttactgc tagcttctta ttcttagcaa ttatacctca cattacatag tattgtgaaa  13740
ctcactatat tcagtgtttt gcctgacaaa catggtatgt tataggatgt gtattcagtt  13800
atagctaaaa ataaattatt ctcgtttttc aaaatttgct ggcctacctg ttaagctttt  13860
gctttaagac ctgctaatgt ttctcaaact tctgtggtta aatcacctga gtgtctagtt  13920
gctctatgga ttcccaggga cccattcgcc agagattctg atttggtaat tttgggatgg  13980
aactcaggga tctgtaaatt ttacaagcac tcagaaatga aacatagact ttaaacagct  14040
aagagtgctc atcaggatta tgttgatatt attttttaaa cagatgtgcc aagcctttaa  14100
tttgaatttc cagggttggg atttggcctt ctatatttgg gggaaaaaag ttctattgat  14160
gattgtggat atataccaca ggtcaaccat tgaatagtct agtcagtgta gttagtgtat  14220
tttataatta ctaagttcta agtatgtggt gtattaatgt cttaggaggt ggatatattt  14280
cctgtatttg taaagcattt gggtaggttt tttaaagaga aaagtatgta acaaactagt  14340
tttgagcgtt gctcttttac ttctttgggc atttttgaag aacacgttaa gtatcttctt  14400
agagcagagg ggctcagagt ggtccccaga ttatcatcat tggtaacacc tagttggtgc  14460
attactaact tgttagaaat gcacattctc aggcgccatt cagacttcat aaatcagaaa  14520
ctctggaagt aaggctcagc attctgtgtt tttttttctt ttattatact ttaagtttta  14580
gggtacatgt gcacaacgtg caggttagtt acatatgtat acatgtgcca tgttggtgtg  14640
ctgcacccag taactcgtca tttaacatta ggtatatctc ctaatgctat ccctccccgc  14700
```

-continued

```
tccccccacc ccacaacagg ccccggcgtg tgatgttccc cttcctgtgt ccatgtgttc  14760
tcattgttca gttcctacct atgagtgaga acacgcggtg tttggttttt tgtccttgcg  14820
atagtttgct gagaatgatg gtttccggct tcatccatgt ccctacaaag gacatgaact  14880
catccttttt tatggctgaa tagtattcca tggtgtatat gtgccacatt ttcttaatcc  14940
agtctatcat tattggacat ttgggttggt tccaagtctt tgctattgtg aatagtgcca  15000
caataaacat acgtgtgcat gtgtctttat agcagcatga tttataatcc tttgggtata  15060
tacccagtaa tgggatggct gggtcaaatg gtatttctag ttctagatcc ctgaggaatc  15120
gccacactga cttccacaat ggttgaacta gtttacagtc ccactaacag tgtaaaagtg  15180
ttcctgtttc tccacatcct ctccagcacc tgttgtttcc tgacttttta atgatcgcca  15240
ttctaactgg tgtgagatgg tatctcattg tggttttgat ttgcatttct ctgatggcca  15300
gtgatgatga gcattttttc atgtgtcttt tggcagcata aatgtcgtct tttgagaagt  15360
gtctgttcat atcgtttgcc cactttttga tggggttgtt tttttcttgt aaatttgttt  15420
gagttcattg tagattctgg atactagccc tttgtcagat gagtagattg caaaaatttt  15480
ctcccattct gtaggttgcc tgttcactct gatggtagtt tcttttgctg tgcagaagct  15540
ctttagttta attagatcct atttgtcaat tttggcttct gttgccatgg cttttggtgt  15600
tttaaacatg aagtccttgc ccatgcctat gtcctgaatg gtattgccta ggttttattc  15660
tacggttttt atggttttag gtctaacatt taagtcttta atccatcttg aattaatttt  15720
agcataaggt gtaaggaagg gatccagttt cagctttctg catatggcta gccagttttc  15780
ccagcaccat ttattaaata gggaatcctt tccccatttc ttgtttttgt caggtttgtc  15840
aaagatcaga tggttgtaga taagcggcat tatttctgag ggctctgttc tgttccattg  15900
gtctatatct ctgttttggt accagtacca tgctgttttg gttactgcat ccttgtagta  15960
tagtttgaag tcaggtagtg tgatgcctcc agctttgttc ttttggctta ggattgactt  16020
ggcaagcatt ctgtgttttg agaattcttc caggggactg tgatgaaaac tgacgtttga  16080
gaaccttcat cttagagtaa aaactttaca tacacatttt tgttgtttta tttatctagc  16140
acaatacttc tttttttttga aatggagttt tgctcttgtt gcccaggctg gagtgcaatg  16200
gtgtaatctc agctcaccac aacctccatc tcccaggttc agttgattct cctgcctcag  16260
cctcccgagt agctggggtt acaggcacgt ggcaacatgc ctagctaatt ttgtattttt  16320
agtagagacg gggtttctcc atgttggtca ggctggtctc gaactcccga cctcaggtga  16380
tccgcccacc tcagcctccc aaagtgctgg gattacaggc gtgagccact gcacctggca  16440
caatacctta tatataatca gggctcaaag atttgttgag aggctcaaca ccaattctgg  16500
accaggaaag attttattta tatcactagt caggaataat ctaaaaacaa aaagcacatt  16560
cttcttacaa gtaatatttc aatacacatt aatgtaaaca catggaaaag tattagctac  16620
ttaataaatt aacatgtaaa tgaaaaattt acacattatg gctatttcag atgtgatata  16680
gatttcattt tcagaaggaa ccctccaatg taaaacagtg attcttttcc ccgtttattt  16740
tactgcatta gaaaatcaca tttaaagtaa gcattttggt gaggtttgga aggtgaataa  16800
atccatcttt tctttaatta tggatattta agagagatgt tgttgtgccg tttagataat  16860
aatgatctaa accaagaaat ttagttgctt tcaaaaataa aataagtgta tgcattctga  16920
acatttttct ttagaaacaa accatttcat ctgttttttt gaatttcaaa ttaattatac  16980
agaattttca aaatttgaaa attaggttag catgagaaac tgaagatact gaattatatt  17040
```

-continued

```
gcctgttcag tctatacttt tctttaggat atacagtagg aaagaaatat gatagttcaa 17100
gttagattac tacttctttc agagtttttt gacaaatgca ggtacagtga tagtgtcagt 17160
tcatggtgaa tttttgttaa aataaattac aaaaaatttg tgatcctggt atcttgaaac 17220
tagttaatat ttgtaaactt tgctaacact gtatatcact gtattctggt tttatctgtg 17280
catctatgag ttatatgtgt gtatagctac atatgtttat atttatacac atacattaca 17340
cacaggagtg gaatcatact caattttttt tgtatagcct gctctgttca tataatacta 17400
tattgtagca tctagtataa gcaaagatta atttttgtag actttgcttt tatcctgaaa 17460
ttttgtggta gctggtttaa tggaaagaca atttctgtga cgtgttttgt cagttaggga 17520
ttgaccctgg taaaatattg ctggataaca acaagcaatg taaaaataca tttgttccat 17580
aagataacct ccgtgaaggt agagacttgg tctgttttgt ttattgcacc gtgtcctgtt 17640
ctgggaagag tgttagactc atagaagatg atcaagaaat attttttgaa tacatcaata 17700
acattctcta acatgtgggt atcctaaagg tttatttttta aagtttattg attagaattc 17760
agaagatatt ttcccagata aaataataga ttgctagctg tcttgaaaat gtaatttata 17820
tttaatttga aatgtcaggt ttttgctatt ttttccatta agtagagata gggtttttaa 17880
aaattacatg tgatgtttta agtattctgg ttttgcaaca attactagat agaaaatgta 17940
acaacagatc ctattaataa tacttccaat aatacatata aaatacttgt ctaaaagtaa 18000
ccctccttaa aaaaacaaag ctggccaggc gcggtggctc acgcctgtaa tcccagcact 18060
ttgggaggct gaggcaggcg gatcaagagg tcaggagttc aagaccagcc tggccaacat 18120
agtgaaaccc catctctagt aaaaatacaa aaaattagcc gggtgtggtg gcaggcgcct 18180
gtaaccccag ctactcagga aaatcgcttg aacctgggag gcggaggttg cagtgagcgg 18240
agatcgcacc actgtacttc agccttgggc aacagtgcga gactctgtct caaaaaaaaa 18300
aaaaaaaaaa ggcaatagga ttaggtatca acttaatgaa aacttcgtga cagcactttc 18360
ttgaaaaaga ctgtggaaac caaagttagt aaactcctgt ttctgcctgg gttcggaaaa 18420
cataaagatg ataaagatgt ttaagtattc cttttttttt tttttttttt ttttgagaca 18480
gtgtcttgct ctgtctggag tgcagtggca caatcacagc tcactgcagc cttgaactcc 18540
tgggctcaaa taatcctcct gcctcagcct cctgagtatc tggaactaca ggagtgcacc 18600
attacactcg gctagtaatt tgattggtta agaacattaa ctataactca cacattttcc 18660
tgaccacatt tgcttaggac aaaacagtaa aagacatgag tgtagatgaa agcgataagg 18720
gaactaatct taaacactga acctcttttc agcaaattgg ctttctagtt tctcagctct 18780
ctctttacac ctctaaatct ctttcctggc aagatcattt atttgccttg gtttatggtg 18840
atactcttca ttgttatact ggtgggtgat tgttttaatt gatagctgtt tttttctact 18900
tcaggaagat gacactgctg gctctgctgg ctctgatgtt taccttgtgg ctaatgcctg 18960
tgtttgcctg tgttcacatt tattccacga ttcatttgtt aacatttact aagctgcttt 19020
tctgtgccag gaacttggct agataaataa atggttgttt ttgtacacag aattagctgt 19080
cataatcagt tactgtagca tttattcttg caaaaatata tatttatact tcaactagtg 19140
atcgaatctc aacttattaa ttcatacatt cagccagcac ataattgaat acttcttatg 19200
tgtcagaaac tgttctaggt gcttgggatg ttcattgaac aaaatagaca aaagtctccg 19260
cctctatgga acttactttc cagtgaaggt gtggattggt gggatagaaa ataaaataat 19320
caagtaagat atgtacttag gctttcataa aaatacagca gggcaagagg accaagatgg 19380
aggcagtgat cagggaatct caatgagggt gagactgcga caaagacttg aaaaaggtgg 19440
```

-continued

```
agaagcaagc cttgtgggta tttagggtag cagtagtcca ggcaagggga acaactagtg  19500
caaaggctct aggaggcaat gtgtttgaag tgttttaaga acagtaagga ggctagtatg  19560
gttagaacag aatgagcaaa gggggcaaag tggtagaagg tgagatcaaa gaggtaatga  19620
ggccattgtg gaggcccata tggactattg gaagggcttt ggcttttact ctaaatgagg  19680
caaaaaccat tttaagcaga gaggagtgat atgacttgat ttcttgttaa aaggattatt  19740
ctagttgctg ttacagaaaa agattacagg ggtgcaaaga aacagggaga caaaagaata  19800
taagattttc actgtaactt atatctagta tgcttgctta tacttgaaaa tgcatatcca  19860
gataattgta gtaaattcaa atattatgtt tatttaatag tactaacatt gatatgctgg  19920
ttaattatga ttaggagcac taataaagca caaatcaggg attcccaaaa agaatgttga  19980
aagggcagtc agcttttcct gtgccagaaa tcaaagtcat agcagatttg gggcaaatat  20040
gtcaaagtca aacttacgca catcactact gagaagacaa agatgaatgt gtgacagttt  20100
cctgcccccca agaatcttta agcattgtga aggaagatta atatagccaa ataactagag  20160
tgatcagttc taccagagag gaccagtttt ggaagccaga ggaaaaaaaa aaaaaacaga  20220
aacaaaatga tgtttgaatt aaatctttaa aagtttctct tataaattta ccaagccaca  20280
tattgggaat ggtaccccag gcagaaggag tagagtaagc aagccagaaa ggaaatacta  20340
tggtgctttt gagtaactgc agtgtggctg aagaatgtgg aaaatgatga ggataaagag  20400
gtggacaggg aactaggtaa gggagggctt ccttttaaat aattagacct tgtcctgtgt  20460
acatttaatg ggattttaat caggccataa tgccaaattt ctttacttcg gaaggatctt  20520
tatggtgatg gtttcagaaa gaaattaaag cagagtaaca gtggttagca ataatgatca  20580
gctagtggtt cccaaactta cgtatcatat gcatcttgga agtttttaaa aactcagatt  20640
ttgggatcct gacttagatc tactgaatca gaatttacag attcaaattc ccagtgaggc  20700
ctaggaattt gaaatgttga atgtccttca cgatgcagct agacaagcat ttgggaataa  20760
agcattaggt gactatttca gtagactaag gagtgggagg ccatttaagc tcaaaggcta  20820
ttctacttct cactatattt ctagtaccta gcacagtgca tggtacttga tagatgcatc  20880
ctttctccca tacctcgccc tacacatctc ttcatgtgta tccttattaa tatcctctat  20940
tataaactgg taaacatgtt tccctgagtt ctgtgagctg ctccagcaaa gatgggtttg  21000
tgagaatccc aacttttgaa gcctgtcagt cagaagttcc tgaggccaga cttgcaactc  21060
ctgttgaggg ggcagtcttg gggactgagc cctcaacctg acactgtctc caggtagata  21120
gtgttagaat tgaattgaag gacacccagt tggtgtccgc tgcagaactg attgctcacc  21180
tggtggtgga gagaacccct cctctcccga tagggttgca gaagttgtct tctgtgttgt  21240
tgattgctgt ggtgtgggag cagagggggg aaaaaagctg ttggagagtt ttttccaaaa  21300
caataggaga ttatttagat ttataaaaat agaatcaaag tagattaact gagcacattg  21360
tgaaatatag agtagagctg tgtgtaagga gtatatctta atgtcaagct gacaccaaat  21420
tgaatgtttg ctggaacgtt caaaaatcta agcttcccaa atctgtgaaa acactcaggt  21480
tagtaaacag tcttatgcaa acagcaagac aatgctcaaa gccatttaag gaaaaagaac  21540
agtaactgaa ttctcttatg gaaatgtgag atgttgtttt agtaagtact gatggtgtta  21600
tactttttgt ttattcgttt gctggtattt cagttcctaa aattccttca aatatgctgc  21660
aaaatacaaa ccaagaactt ggtggatttt ccatttgttt tcctgtggga aatgatggaa  21720
ttaaaaacct tgaggattag accttgagag ttaccttcca gtgtttatgc caccattata  21780
```

-continued

```
caaaattctg gaggacaaaa cccttcccac ttaaaaacca gttagtttca gaaaatcacc  21840
tcatgttagg agactgcatc attatagtat gtgtgttagc tttaggtata gatctaaaat  21900
atttttaata ttttaaaaac ttaagccttt cttcattaat ttggcctaat acaagttaga  21960
ataactttaa aaatgagtac aaacaacaag gaagggccag gcgcagtggc tcaacgcctg  22020
taatccgaac actttgggag gccaaggtgg gcagatcacc tgaggtcagg agttccagac  22080
cagcctggcc aacataatga aaccccatct ctactaagaa tacaaaaatt agctgggcgt  22140
ggtggcacac gcctgtaatc ccagctactc gggaggctga ggcaggagaa ttgcttgaac  22200
ccaggaggca gaggttgcag tgagccgaga tcgcgccatt gcactccagt ctgggcaaca  22260
agggtgaaat gccgtctcag gaaaaaaaaa aacagtttct gtgactgcta gacaaatgtt  22320
gagcaagtaa aacaccaaca atgttgaact tagatattga aatagctgct ctgtacaaat  22380
aaagtctact gggagtatag actgaattac catcttttga ctctttcgcc ataatgattg  22440
gcattaccgg aagggattac cttgctttga agagctgctg gacagtagag cagagagcat  22500
ctattaccat tgtaggtgcc tttcagttag gattttggat ttataagcaa actccaagaa  22560
agagcctggt tctgagtttc tctgaatagc ttaggtcaag tcctaaattc tgaagccaac  22620
tcctataatt ccttctttat gtctttggca tgtgaagtag gcaaatttcg aactttataa  22680
taatagccta gacttacaaa tacttgcctt ggtaatcagg atgagttttt gagagacaac  22740
atagtctagt gttaatcgcg tggacaccag actgcttgag tgaaatacag gttctaccat  22800
ttattaacgg agtaatgttg ggtaagctat ttagccaggg tccttatctg taacatggtg  22860
ataataataa agattaaata ataggtgaaa aatgtttaga ataccactgt gttattagta  22920
agcaccatgc ataggtgttt ggatttaaaa atactggcaa aggccaggtt gggtggctca  22980
cacctataat cctcgcactt tgggaggcca aggcagaagg atcgctttag cccaggagtt  23040
caggaccagt cgaggcaaca tagattccgt ctctgcaaaa aatttaacag aattagttgg  23100
gcatggtagc gtgtgcctgt agctacttgg gaggctgagg tagggagggg gaggattgct  23160
tgagcccacg atttcgaggc tgcagtgagc ttatgatcat gccactgtac tccagcttgg  23220
gtgacagagc aagactctgt ctctaaaata aaatgaaaat aaaactgcag gcaaaaatgc  23280
caactgaaga gtgaacatga acttttcttt gcatttttct tgggcctgag actttaagaa  23340
gtgcagggca gttaaaatga tgagatataa ttctcaccta tcagctcagc agaaattaat  23400
aagattaaaa agatgcgtaa tatataatat tgcagagtgc atgggggaat tgatatacac  23460
attcatgaac tggcagagac aaaaatgggc acagaaccat ttggaaagct attgtgtatt  23520
ttaaaaaatt tcagtagcac attttttata tcatgaaatt tcacttcaga atgtcagtcc  23580
tgtagaaata ctgacgcaag tgcaaaaaca acaaaaacca acttgtacct tcaaggccag  23640
aaagagttat ttcaccaaat aacataattg aggtacatta actttattag aagtaaatct  23700
gataatctgc tcacatttta aatagttatg gtttaacttc agttcttgaa gtcacatatt  23760
tttacaatta ggaatgctaa caggcttttt gtgcaatacg aaaagatgac tttaaatgcc  23820
tacaattatt ttgtgtcctt ttattttttt ttaattttta ctgacctact acaaagcact  23880
aaatatttta tgttcttaat ctgaagaaca atagacattc tctataaaac aactcttgct  23940
tattcatgaa ctttgtacac aagaagctta ataagacggg ctcaaaatta tttttctaaa  24000
tatatttcct atacaaaata atttcaagat ataattgtta cttttgtgtc taatactgta  24060
tgttaaataa taaaatggta agcatgtaaa aactacaata ccacaaagat tgagctattt  24120
tgccagtagt atactccaac tttagttcta gaacagttgt agaaatgggt aaacaaactg  24180
```

-continued

```
ttttaactgt actcttaact gaaatatagt accttatgca gtagcagaac atatcagcag  24240
aagaacttca cttgacctgt acttaaaaac aaaacagatg caatttataa aatttagaga  24300
aatatagtga ccttatttgc atgtggaaaa tgtacttctt tctgatctac atatcttctg  24360
ttgtgcaatg taagcagtaa aacaaatagt acaggattca tctctgtggg acctagaccc  24420
cctggtctaa caaataattc ttggtcagta ctgtaattct gtggtataaa actgataaaa  24480
ttagccttcc tgtgactaga caagaagccg ggcagtttaa atgctgaaac tcacaagaac  24540
ttcagaagct ttagctttaa gctttaagct tacttagaaa tgttataaga cctccagtag  24600
tcacatatga agaatatcat gaagattttt ccattaaatc tttattatag atcccttgat  24660
tggtttctgt ctagactcat tgtgtgataa aggacataat aatttttatc accttcatct  24720
aatataggtt tgtcaactct atattagttg ttttcttgaa ggctggtttt cttccaaaat  24780
tcagtcttat tttcagtcta cactagcttt taaatatact gtcctttaga tgctttatct  24840
aacctcaaat ttctaatgga tttgtcttag acacttattg ccactcctta gatagtcatt  24900
gctatctttg aagttctgga cgatacgtgt attacagagg aactggagac attccatcac  24960
catagttagc ttgattggat accctttaaa agcatatact cgcgcctgta atcccagcac  25020
tttgggaggc cgaggcgggt ggatcacttg aggtctggag tttgagacaa gcctggccaa  25080
catggtgaaa cctgtctgta ctaaaaatac aaaaattagc ctggcatggt accacatgcc  25140
tgtaatccca gctactcagg aggctgaggc aggagaattg cttgaacctg ggaagtggag  25200
gttgcagtga accaagatct tgccattgca ctccagcctg ggtgacaaga gcagaactcc  25260
attaaaaaaa aaaaaaagca tatatagcac atattataag gttttcaatt ttttcaccaa  25320
gtgtttcatt tgggtagtca tttattggta gtttacatca gttgagtggt tcagaaaaaa  25380
tacagtaagt tgcttataaa attctgaaca ctttggccag gcacaatggc tcaagcctgt  25440
aatttgagcc ctttgtgagg ctgaggcagg agaattgctt gagcttaggc gttcaagacc  25500
agcctaggta acaaagaacg cctggaatga ttgtggcatt tgaactaata ttcaggttta  25560
acaagagata attgaccatc actctatttt agaggcttta tttgaaccag atagaaatct  25620
atttcccaca gctatcactg cctgtcacct acaacttaag gggttgggg aggaagtgag  25680
agattttctg ttagggccaa tagggacctg ctagataccc ccccatcctg ggaatggtgt  25740
atggaactcc agtgtatgct ggagttatta tcatcatact tgttttttta ttttactctt  25800
ctgcttatac agatcaagtc ttacgtttta tttttaagtt taaattgaaa acatttacag  25860
agaacaatgc agtgaaatga aaaaattaca gactgctggc atttgcattt tcatgtagcc  25920
tcagtgacta attttttttt attgtacagc attgagaaaa tcctagttca tataactagt  25980
tatagttcat atagattcat ataactagtt ttaagtgata atagtttctt cctttttttc  26040
ctccaccatc taaccagatg aagataatag tttttaatag ctcaccgtaa atttcaaggt  26100
actcaagtta aattgatcta gatgcttgag ttgaaatttt tctatcaaag ttcaataaca  26160
tgcttacatt ccttattaaa gtataaaagt cctataaaca cacaaacttg agtaagtact  26220
aaaactagta tcagtattgt cacaatacaa catgttatat tgtaacaaga gcatttgctg  26280
agaactgtgc ttgttactcc agaatgttgc ttctatggtt gtacctttca actttgcaga  26340
tcatttggaa ggaggagaga tttggggtgg agacaattcg gtacttcatt cacaggatgt  26400
aaggaggatt aagtaaaata atgctggcta aaagtcctta tttagcatac tgcccaatgc  26460
tcactaaatc ataatagctg tttttaacat ttggtgaaga atctatttaa caggagtgag  26520
```

-continued

```
ttgaggggca taggagatca tgtgagtgtt taaagtagaa gcagcattcc ccattaagaa  26580
gagaaatact gtggaagagc aaagacttta aaacacctgg gttcaaatcc tatttgctac  26640
ataatggcta cttttaacct attgaacgcc agttccctca tttgtaaaat agggacaata  26700
tttaacctat ttacaggttg tgagagaact aggcacctag tacagggtaa tgttggcaca  26760
tggtaacctt taataaactg ttgctattca acaagctatt agatgtcact aggcagttaa  26820
gcaaaggaag acagcttttg cttggtgtga caatgaaaat ctttctgatt tccttcttgg  26880
aagagttccc tgaagatatg tcattgtatt gacaccttta tttttgctaa cctatccctc  26940
taaattctgg atattgtgtg tgccacagct ttttttcttc catattcctg catttatttg  27000
gcacctgttg tgccagtaat agataagggg ctgctaaggg aggaggcaac ctgcactggc  27060
ttatagctgc taatgtcagt tcctatagct tatcgtcagt gttattcatg tggtaaaagg  27120
gtgagaaagt actggagtct aaagaaacaa gtagaaatca gtttgtagct attaccgttc  27180
tacctgctaa caactcctgt tttcaagtta ttatgtacaa ctttaggtag tttctctagc  27240
cttaatcgtg gtttctctgt attgagacta cttttgaatt ctatgaagta cagccttaga  27300
tgtacaggct actttaaatt tttgcctaaa ataaaaacat tctctccaat tacatatgct  27360
ggggaggaaa cacctgcttc cgacaggttt aaagcttggt tttggacttt ttgtgagagt  27420
tccttatgtg tgcagtaatc caaaatttgt atagttgccc tttataaaag tacattaatc  27480
tagtagacaa atctccatgt aacttaatta catggcatct tctaatcctt ctgtgataag  27540
cagaaatgta aagttttatt caagttaagg caaactaact tgtatacact ttccatctcg  27600
tgtttttctt gttgttgtta agtaggataa gttctgaacg tcgaaaagaa aagtctcgag  27660
atgcagccag atctcggcga agtaaagaat ctgaagtttt ttatgagctt gctcatcagt  27720
tgccacttcc acataatgtg agttcgcatc ttgataaggc ctctgtgatg aggcttacca  27780
tcagctattt gcgtgtgagg aaacttctgg atgctggtga gttattttac aagggtataa  27840
ataggcctga aaattagaag ttagaagtaa atagaaatta tttttagaag gtggtcgcaa  27900
tgttttgatt ttgtatacct ctttatattg tgatatgtac acgtttaaaa atttttctgt  27960
aattctcact atttttatca agcttcattt ttttctcatc agttattctt tgaaataatc  28020
attctttatg cacataattt gttttgcttt attctcttaa acatactctc aattcttttc  28080
taatataaca tcctttttat tacctgcttt taaagcttta gtcaggaata agatactggc  28140
ttttcccctc ccccctttt ctcctgttcc atctaccttt cttcctttaa aaaacatgac  28200
tcaggccggg cgcggtggct cacgcctgta atcccagaac tttgggatgc tgaggcgggt  28260
ggatcatgag gtcaggagtt caagaccagc ctggccaaga tggtgaaacc ccatatatac  28320
caaaaatata aaaaattaga tgggcacgct ggtaggtgcc tgtaatctca gctactaggg  28380
aggctgaggc aggagaattg cttaaactca gagggcggag cttgcagtaa gccgagatca  28440
agccactgca ctccagcctg ggcggcagag tgagactcca tctcaaaaat aataaaaataa  28500
ataaataaat aaaaaacatt actcttcttt cttcttctat ggtttgcttt gctgcattac  28560
tttaatcatg aaaagcagct ggcacatcta attatagttt ttctagcttc tggcctgcac  28620
ttttctgtgt tgaaatggct gtatatatta aataaagtgt ctgcgagaaa actttgtaaa  28680
aacatctaaa tattatatca tttaagtaca actttttaac taattatttt cctcttcttg  28740
tgcccttttt aggtgatttg gatattgaag atgacatgaa agcacagatg aattgctttt  28800
atttgaaagc cttggatggt tttgttatgg ttctcacaga tgatggtgac atgatttaca  28860
tttctgataa tgtgaacaaa tacatgggat taactcaggt aaaatgcaca catattaaga  28920
```

```
gctcttctat atgtttttat gattttatga tctagcccta atttttaaaa atgtgtttac  28980
agtttgaact aactggacac agtgtgtttg attttactca tccatgtgac catgaggaaa  29040
tgagagaaat gcttacacac agaaatggta agaaaagtct gttgtttgat ttaatgtgac  29100
aggtggtttt acataataag atactattgc taattattaa actttgctat tgtacttacc  29160
caaggcaaaa tgttatttca tgtttaataa aatgtctatt ctttgttaaa actattattt  29220
tagtttttag gaatttcatt ttgaaagccc acctaattgc ataaataatt gtgtgggtgt  29280
gagaaataaa atggaaaagt aaaatcatga ccaagagagt tacaaataac tttttttttt  29340
ttttttaag atggggtctc gctcttttgc ccatgctgga gtgcagtggc acaatcagct  29400
gactgcagcc ttgaccgctg ggactcaagc gatcctccca cctcagtctc ccaagttagc  29460
tgggaccaca gacgcgtgct accatgccca gctaaatttt taaaaattat ttgtagagac  29520
aaagtctcac tatgctgctc aggctggtct tgaactactg ggcttaagcc atcctctcac  29580
ctcggcctct caaagtgttg ggattacagg catgagccac cacgcccagg ctaccttttt  29640
tttcctttc tttttaaatt gtgatagggg ttcttgctgt attgcccagg ctggtcttaa  29700
actcctggac tcaagtgatc ctcctggctc agcctcccaa agtgctagga ttataggcat  29760
gcgccaccac acctggtgga gttaaaaatt aaaatacacc attaaggcaa ggagaaatta  29820
taatacaaat ggcagataat aggactttag acagtcatta aagttgaggt gccagtttga  29880
gtctaaggcc caataaaaaa agttcaccag aattttaaga caaacaactg cttatttgac  29940
ttctttggat gttctcaata attcgagacc gtgtagttag attataaagt attacattgt  30000
ggatgcccac atattaacaa aaatagagag taagacctct aattcttagg aattaattgt  30060
taaaaataat caagtgttcc aagatttttt ggaaactacc tcttgaatta aaaaattaaa  30120
gtctttctac atttttatct tgttaaacag tgtatactga tcataattat ttaaaaaatc  30180
atgtgttcta agatttttgg aaagtacctc ttgaattaca aaaacaagaa agtctttcca  30240
catttgtgcc ttcttaagca gtgtatactg atcataattg aacttttctt catgatggaa  30300
agttaccaca aggaaaattt cttatgttct gctgttcttt gttgctctcc aatttaagtg  30360
catacgtttg tttgcttcta tattataaaa cctcaaattt actttttgta taatttttga  30420
ggttttcttt ttcatctcat ttattataat aatagctaac ctccattgag agaatgctgt  30480
gtgccaggac actgttcttc ctattttata tgcttttaac tcctttattc ctcacaacaa  30540
ccctgtgaag ttaactgtta gacaatttct attttactag gaaactgagg tacagagtta  30600
ctaagtaact ttcccaacat tatttggtta gtaaatggca gagcttgggc tgaacttcag  30660
tagactggct tcagagtcca cgctcattag tcctttggag cgcttttcat attcttgaat  30720
tctcacattc tgtctttttt cactctgtca gcaggacctg actcctgttt ttaaatttca  30780
tattgtgttt ttactgttaa tttggaaaac aaatgcatac tttttagaat tctgtataaa  30840
ggaggagtaa atatgctgtg aacaaggacc taagtgggtt gtcaatgagt ttaatatatg  30900
agttctaatg tgcagagttg aggtttatat tgactgctca gtgcttccct ggggctagac  30960
tataaatgga tggatattag gaagtcttgt tctgatttgg taatgatgtt aatgcattat  31020
tctaaatcag atagtcttaa tatagtttaa atgtatgttt cgaaccaaat gttctttttt  31080
aaagcacaca aacattttga aatcattact aatgtggtta atgaattatt gatgttccat  31140
tgggaaacta aaatgcagat tttctcttt tagaaatcag ggactattgc aaagcatcac  31200
attttagtga tacactgaga gccagtggtg tgtttataca aatagtccta ttttccaaat  31260
```

-continued

```
aaattctaga aaaatgcttt agaatttata aattatacaa aatatgactt atttttagag  31320
agtttaaaat ttaggttttt ttaatggttt gtttttgttt gtttgttttt tgttttttt   31380
ttcctcatta ggaaaacact agtacttttc agttaccttg atttttaaat taatctgcag  31440
gtccccattc aaaggccttg ggttcctttc aaaggtcagt ataattcaag cttagtttat  31500
gaaggactga acatacccaa aggattttgc atgtggatct ttactgccac taccacaacc  31560
atcaacacct acacacacac gacacacaca cattctctct ctctctctct ctctctctct  31620
ctctcccccct ccctcccgca ctccttccct tccccctcct ttgctctcat ggcatctttt  31680
aaaaatatac tcttaaatcc ttccagggag ggcaaattca cttcttaatc taagtaaacc  31740
caaatggcat gcatcagcac caggactgcc catctttcct agttccatta ttcatagagt  31800
ataggctgga attcatcttg ttcctcaaga gtccagcatt tctagttaac catgcctaca  31860
tttaaactta ctctcatttc ttttctactt tacagtgttt tttcaatata ctagcattac  31920
agtttccaga tttgatttct ctcctgtctt atttccatca gttttcaagt ctattaagat  31980
tctacctctt catttgtctt ttgccaccat tcttttccct catactctac tggctcagcc  32040
ctctcattac agtcacctaa ttctaacata tatattgctg ctaagttaat tttccttaag  32100
ttactgattg tgctttttta aagccccttg ttgaatattt aggcaggact ccatgtggac  32160
atccacagcc ctccgtggta cagccctaac cttcccttct agctttgcct tactactctt  32220
ctacgtgtac tctacattgt ggacaaacta ctatatgctg tttttcaaac atgtcctatt  32280
tttcctacct ctgtgctttt cattctctta cttctccttg gaataccctt ctaacccatc  32340
tctacttact gacattctaa tgtctctttt tctaagcaag acttcttgat ttcccttgac  32400
tagaaattat cttctaagct ctccctatcc ttctttaaag catttttata agtctcaagt  32460
accaactcta cattgtgttt ttgttgacct tactatatct actacatttt taacttcttc  32520
aggaaaggtg gcgtatctta ctcatctttg tattgcctac aatatctagt ccaggttctg  32580
aataataaat atttttatat gtgttctgaa gcacactgac caatgaagat aagaaatcaa  32640
gaggctagtt ccttattttt tttaattttt tttttgaga cagtgtctca ctttgtcacc   32700
caggctggag tgcagtggca caatctcagt tcactacaac ctctgcctcc cgggttcaag  32760
tgattctcac gcctcaacct cccaagtagc tgggattata ggcatgtgcc accacaccta  32820
gctgatattt atatttttag tagagatggg gttttgccat gatggccagc atggtctcaa  32880
acttctgtcc tcaagtgatc ttcctgcctc agcctcccaa agtgctggga ttacaggcat  32940
gaggcataag ccactgcgcc cagcaagatg ctcttttctc agtcacctaa atataatctc  33000
atttttagtt atagaaggtt tgaaattgga gtgaatagac tttacttaat tctgacttta  33060
tttctgtagc tttttttttt tgagatggat tctcgctcta tatcccaggt tggagtgcag  33120
tggcacagtc tcagctcact gcaacctctg cctcccacgt tcgagtgatt cccctgcctc  33180
agtctcccaa gtagctggga ttacaggcac ccactatcac acccagctaa tttttgtatt  33240
tttagtagag acagggtttc accatgttgg ccaggccggt ttcgaactcc tgacctcaag  33300
tgatcctctt gcctcagcct cccaaagtgc tgggattaca ggcatgagcc accgtgccct  33360
gcctatttct gtaacttttg ataagtcatt tgatctgttg ttgttgtttt ctcatagtaa  33420
caaagtagaa gtaattttct gcctgcttta ctagataaat taaggggaaa aaaataagat  33480
acgtaaaaat gttatttgtt attaaaaaga aagttgttat tttaaaggtt ctataaagac  33540
atagagtgct tattagaaat tgagctaaca cattcaggaa aggataggaa gagtttgctg  33600
aagttctttc tttagggatt cttgtgtacc gatagcacag ttaaagagca aactcatacc  33660
```

-continued

```
atttttatat ttctgtgtat ttgactaagc ttactggctt caatgattaa ctgttatccc  33720
aaatatggat tatctttcag ccaactcagg gaatcacagc tactgagtag tgtgtgtcag  33780
atctcttggg tgtgctggag tgagtaaaag gggaatgaat tactgtgttc atgctgagac  33840
ttaattgaac gggtattcag ttgatctagg tgatgggcac tttgttactt ttattgtaac  33900
aaatttgtat atttagttgc tttaaaactt tatttcatgc tttcattagg ccttgtgaaa  33960
aagggtaaag aacaaaacac acagcgaagc ttttttctca gaatgaagtg taccctaact  34020
agccgaggaa gaactatgaa cataaagtct gcaacatgga aggtaagtga aaattatttg  34080
tgattgatta tacactttat ttatacatag acattgtagt attaagataa ctttagaatt  34140
gtgagggaag gtttacagtt ccatggtgtt tggttatgta acatttatat cttcaactca  34200
tttgcatgtg atctccaaaa tgcagaaccg tgtagtaatt tgccaatttg aggcacaaac  34260
ttaaattacg tgaattgtgg cactggtgtt ccaggcttaa tcagttggct ttgccagcca  34320
cacaatattt gaatcctgat agggcttaat tttctattaa tcatggtttt atatctttgt  34380
tcaatgttga aacatagtca tcagtgcaag aaataactat caaacagcca tgatgatgag  34440
atgaatgaaa aagcagccta gactttatac gaggggaatt ttttaaagag taatgtatag  34500
gccctgggca ggaagtaggt cataggtggt atcataggaa aaatgttcat tgattttcaa  34560
aaacgtgatt aatccactag tgacagtaaa ttttatcaaa gcttactggc catgtcagac  34620
tcaactactt atctctgctt tttttttccc tagcattgta aatatttttt ttaactgctt  34680
tgttcttcat acacaggtat tgcactgcac aggccacatt cacgtatatg ataccaacag  34740
taaccaacct cagtgtgggt ataagaaacc acctatgacc tgcttggtgc tgatttgtga  34800
acccattcct cacccatcaa atattgaaat tcctttagat agcaagactt tcctcagtcg  34860
acacagcctg gatatgaaat tttcttattg tgatgaaagg taaattagat ctaaaatgtg  34920
aatttgaaat ttttaattag tctacagcat tactgaatat tcaccatagc aaagattcag  34980
cgctggccat gcatggtggc tcacacctgt aatcccagca ctttggaagg ctgaggcaag  35040
cggggggtgg atcatctgag gtcaggagat tgagaccagc ctggccaatg tggtgaaacc  35100
ccatctctac taaaaaatac aaaaattagt gggacgtggt ggcaggcact actcaggagg  35160
ctgaggcagg agaatcgctt gaacctggga ggtggatgtt gtggtgagct gagctcacac  35220
caccacactg caagcctgga tgacagagca agactcccat ttcaaaaaaa aaaaaaaaaa  35280
ttactcaatg ttaaactata ctttccacta aattgaacag aatgatacat cctataatat  35340
tagattaact ttgtaaatta attcagccac atttattgaa catttactct gtactatgaa  35400
cacttacttt actaggtgct atccagaagt taagatgagt cttttttttcc ccaatagggg  35460
ctctacttac ttagagaatt tcaaagatat gcagtgtgta ttttgagcaa agatagatta  35520
ccttaggttg gggactagaa agccaagtgt ttgtacatct cttcatccta catattttcc  35580
ctgagaagct tcaaccttgc ccatggtttc tattactatt tcccacattt cttcctgtaa  35640
ctaattctat ttaattgcca acttaatatt tctatctgga tattcttctg tattgtaaac  35700
taagtattac tgtaacaact gtactactac tgccccccaaa caacatcatc atcaaaaact  35760
gcctttcttc ctataatgct tattgtggtt taatacacca ccatacacac atgactccag  35820
caaaactttg gaagtcatct gtaacttttc ttttacattc attggctaca tacagttggt  35880
gtctaaatct tacagattta ctatctacat atatctcttg atccatttcc tcctttccat  35940
ccttgcactc ctgccattga attcattagc tcattattac tcttgacttg agttgttggc  36000
```

-continued

```
atagctgcct ttttgccaac agatttgtac ccttataatc tttcatctaa gttgccagaa  36060
agtgggtgtc ctaatgtgaa aatcagatca tgtcattctg ttgttgaaaa tgcctcaaat  36120
gcttccctcc atctttgcac acaaaaatat tttgtttata aaaatactag atgagggaag  36180
taaatttttc atttatcaaa agaagatgtg tattttagaa gactgaaaaa aaatagacct  36240
acacaataca atctaaactt agcatggcaa acaaagatat ttatgctctg gccctaactc  36300
tgtctttgga atcagatgtt agattcactc atggcttgca gctctgatac ttacaatgtg  36360
gccttggcct tggtacttaa ctgttgtaaa attcacattc cttatctata aaataagaat  36420
catggctggg tggggtggct catgcctata atcctagcac tgtgggaggc cgaggtgggt  36480
ggatcacctg aggtcaggag tttgaaacca gcctggccaa catggtaaaa ccccatctct  36540
actaaaaata caaaaattag ctgggtatgg gggcacatgt ccgtaatccc agctacttgg  36600
gaggctgagg taggagaatt gcttgaatcc aggaggcgga ggttgcagtg aaccaagctt  36660
gcaccactgc actccggcct gggagacgga gtgagactcc atctcaaaaa acaaaaacaa  36720
aacaaaaaaa agacctcaga aggatgttgt caggattaaa ggagtccatt gagtgcctag  36780
tacagatagt gaatgcttca ctactggtgt caactttaag aaaatgaata tagaaaagct  36840
aagaattatt ttaaggtgtt tactactagc atgtaaatgt atgatgggac agagatttcc  36900
atcctatttt gaggaattat tttttatttt tttgaaaact taaggtaaca aagtagagag  36960
gaggccaggg agaaaggaag gtagtggagc aaaaatgaga aagggagtga cattcccctc  37020
tagttatagc agaaaattag caaaatgatc atgacaggag gtaacagtaa agacagccag  37080
ctcatatatc aaccaagaca gttttgagtt tgaccagcag actgttattt tctggtttag  37140
agctctttcc aggaacttct tgcatctata acccctgaga accaagctat ggaaaaaatt  37200
ttgctcaatt ttaagaaaat ctaacatatc aagctcctca actccaaaat attccacaaa  37260
tagctgctat ttactatact gagtaataat catttaaaat tattcaacac tttatttgag  37320
catctactat gttcatggca ctaaagtaga aatgaagatg aacagttcct gcctcaaaat  37380
aaatgagtag tatactgctt tagatcatgg gtttcctagt ccattaaaaa cactttttgg  37440
tcatattttc tggacacccc gaccctttttg gtatagaata taacctatgt aattctctaa  37500
agttaaatta acctcacttt tcttgctcta atatgtgtaa aactgacctt ctaggaaagc  37560
atatacagtt tatattttttg acttcttggt atcttttagt gatagacata cctcagattg  37620
agaagcactg attgacatta gattaaatca gagcttccta tgacaatata aacaatacct  37680
tcattaatct gatcccccta cctacttctt cagcatcatc tcatatctgt ctccactaat  37740
catattatag aatctttgtt acctgcacca tgttaagcat ttttaaaaat cttttgttta  37800
taccatacct ttttcctgaa agcggttttg cctttccttt gtctctagtc ataagtctcc  37860
tataagaggc tgttcctcat tctaccattc ctttgcatgg ataggattcc atggaataga  37920
ttctcatcac tgcatttatc acattatttc ctaagtagta cagtacatct actggaagat  37980
tagccacgta ttgagttttg tctttgcatt ttcatgccta gaataatgcc gggcacacat  38040
aggcatatta agatttgaat agtgaaaaag tttttaattc catggggatt ttatttaaac  38100
agaaaaatat aagaccaatt agaattattt ttaaagcata atttcaagaa atatgactga  38160
ttttgtttaa aaacatgttt tcctttataa tgctgccacc tggtgttgct gtgtttagag  38220
atgtcccttt gtaaagaatt gagggtttga gttgagtttg gtttggtttt tggcaaatca  38280
gcttttcctt tgtatattta ttttgtaata aactatggaa gatcttgcct ttaagtgtga  38340
gaacacaagc aatgttactt ttataccttt atagaatatc ttgcctatgt ccttcctgta  38400
```

-continued

```
gttaggtagg gttttttttt tgacacacag catgttatat aaggtttgct tgcacctcgg  38460
taggaaagtc ctctgaaatc taaaggctga gaatctaaaa gcttaactca tgttttgctc  38520
ctagaaagac ttgagaagag agtatttctg ttcagcatgg tactaagaag acagctttct  38580
cttcctcatg tcatggttgc catttcatac tgcttacaga gaataagatc tagtctctgt  38640
cttaaataaa ggtctactct ctgccagcga gctagatagg gtaattggat tgttttccaa  38700
tctattttca tttgaaatat tgttttatct gaaattactc ccataatttc atgtaatgcc  38760
aaaaactaaa ctaagtacaa gagcatcttc aaaaaccaac ataattcctt tagttcccat  38820
ttagtgtaga tgctctttgg ttgatgatat tagaattgtg taatggctat tgatctctca  38880
aagtgaggtg ttgcctaggg gcttaaaagt tactacataa agaatttggc tttatgaaga  38940
aatgttacag attttatcta tattttaaaa taagtgtaag tgactacctt tataactttt  39000
accatgtagt ttagtagtat ttcttatctg tttattaata ccctgccttg ttaccaaaag  39060
tatgtataat gagatgtaat aagaataggt aacaagtagg ctgggcacgt tggctcatgc  39120
ctgtaatccc agtactttgg gaggccaagg cgggtgaatt acctgagttc aggagttcaa  39180
gacgagcctg accaacatgg agaaacccca tccctactaa aaatacaaaa ttagctgggc  39240
atggtggcac atgcctgtaa tcccagctac ttgggaggct gaggcagggg aatcgcttga  39300
acctaggagg tggaggttgc ggtgagccaa gatcacacct cattgtgctc tccagcctga  39360
gcaacacgag ggaaactctt gtctcaaaaa aaaagaccag gtaacaagtt tgggtgaaca  39420
ggattaaaga gttaaataac aggaggaatc tagaggactt aaagaaatgt gtggtgttgg  39480
atttaataac tgtagttgcc aaaggtgagg tgtaaattta ttctaagcaa aggaggatgc  39540
tcatttttga aaattcactt gtccataaga ttaatgccta tcagttaact tgggaggaga  39600
aaaatttttc tttatcagtg tctccctttt ttttcttaaa tcttgtattt tttactaaca  39660
gaattaccga attgatggga tatgagccag aagaactttt aggccgctca atttatgaat  39720
attatcatgc tttggactct gatcatctga ccaaaactca tcatgatagt aagtacaatg  39780
gaagaactca gagatattct aattacttaa ctgttgcaac ctctgtacag tttggctacc  39840
catctaattc tctggttaaa agttctagac taaatgtgtt aacaggccta ttcagtagag  39900
atcttgacca ttttgtgttt tgtatgtgtt gcaacaaata tcagtaaaaa tagaatcatt  39960
taatcataga aaaaacttcc tggcatttta aatacaaaga cttttgaaaa tccaaatatt  40020
atagagtatt gaatagcata attttcagaa ttcacataaa tactcagaac agtggttggt  40080
atgtaaaagg cactcagaaa gtatttgtac aatcaatgaa tgtgaaggtg gtgaacatca  40140
cctttggtaa taagtaccat tttaaaaaat gcttataagt gcatagttag gtatttatat  40200
ttatgggttc atgaaatatt ttgatatagg catgcagtgc ataaggataa atggagtacc  40260
tatcacctca agcattatct tgtgtgacaa acaatccagt tatactcttt tggttatttt  40320
tattttattt tattttattt ttttcttttg agacaggatc tcactctcgc ccaggctgga  40380
gtgcagtgga gcaatctcag ctcactgcaa cccccgccta ccgggttcaa gagattctcc  40440
tgcctcatcc tcccaagtag ctgggattat aagcatgtac caccatgcct ggctaatttt  40500
tgtattttta gtatagacag ggttttgcca tgttggccag gctggtctcg aactcctgac  40560
ctcaggttat ccacctgcct tggcacccgg cctcttttag tttctttaaa atgtacaatt  40620
aaattatttt ttactatagt cacccaaaac aagtaccttt gacataagat ttgattctga  40680
attttactca aatgaatgtt aagatcccca agataagtta aactttggac tatctcacct  40740
```

-continued

```
gtttaatctg tacctatgca tgacttccca ctgtgcttga ggatacctga atatcactga  40800
gtttgtgtga ctgatcagcc ttgaactcaa gagtaaatcc aagtctgcag tcaggacacc  40860
ccaatcctca aaataatacc atcattagca tttatttagt actttctccc aaatcagtat  40920
ttaatttaaa ttgccaaaag acttacaatg tggtatcaat ttatatttaa atatgctaca  40980
tatagctttt taaagcatct ttggttctct ggaaaccata gtcagaattt aaggaagtta  41040
ttgtggcacc attttcttga aaaaggctat tgattattct ctaatctgac accaacctaa  41100
gtcattaaag gaattttagt tactgaagat tgtatattca tgaactcttc acttagctca  41160
ctggcagcaa aggagtttta tttaggggt ttgaaaaagg aaatgggtac attttcagct  41220
attctgggac gcactgtcag aatgtaagca gttacaactg attccactaa ataaacattt  41280
gttttccaaa acaatgatga acattcagca tctgttcatt taattgaaaa ttcaaagtta  41340
aaatattttc tctgcatgat tctttttctt ttccccccta gtgtttacta aaggacaagt  41400
caccacagga cagtacagga tgcttgccaa aagaggtgga tatgtctggg ttgaaactca  41460
agcaactgtc atatataaca ccaagaattc tcaaccacag tgcattgtat gtgtgaatta  41520
cgttgtgagg taagtaagtt tgagaaataa acatttttgg ggaacaaata gtaattcttt  41580
ttggatactc tgttcattta taggaagata agataataaa tattaactaa attttaattc  41640
ttttacatcg ctaccaaatt attattttct atactctgac ctaggtttcc agtccagcta  41700
ttccacagtg atgctgctaa acactgtcag tagttgtcta tccccatacc ttcactccta  41760
tttttaaaaa gaccatgaaa aaaataccag atccattgat tggtttggtc taattataca  41820
gatatcggca tatactatct caagacagct gtgttctttt tgtaggaaga atcctggcct  41880
agatttgtat catagctcta ccactcatta gctccctgac cttggggaag tctcttcatt  41940
tttctgaatt tcatctatgt agataatcct tcagaaggtt ataatgaaaa ttaaatgaaa  42000
ttctatgaga ttagggaggg gggagggata gcattaggag atatacttaa tgtgaatgat  42060
gagttaatgg atgtagcaca ccaacatggc acatgtatac atatgtaaca aacctgcacg  42120
ttgtgcacat gcaccctaga acttaaagta taatttaaaa aagaaaagaa attctatgag  42180
attaataagc tatatgatgt aatacatggc tcttgtatat tcatgaactc ttcacttagc  42240
tctttggctt gtgaatatta tgtacatcaa aatttaattt ttcatttgat ctattttact  42300
agactcctgc cccatctagt ctacctgtcc acattattac cacattctag tccatcttgc  42360
ccattactac caggctaagc tttctagtgt ggatatgtca tcatcttatt ttccttagaa  42420
ttttagcgat ctttttatca tttccaagat aaacacttgc ctaggtgtac agcatccttg  42480
tttaccatca tactcacgca ttagagattt agccttccct ttaaaatcta gggtcactcc  42540
tcttaggaag actttgggca gtttttattt ttgctacttc tgacaccatc ctttaatgtt  42600
ttaatattag tgccacagag ttctttttgtg actttaccat tatgtaagaa tcttccactt  42660
ggaatgtctt tctcttcctc acaccccagt ctgcctagca aatgccactt gatcccaagt  42720
atcagcttgt tagcttctca gtgaagcaag ccttctctat tttagcagtt atcacagtgt  42780
attttaattg tttacatatc tactttcaca atgggttata aatttcttaa ggtcaagggt  42840
tggctatttt aatctttgca ttatcagttc atttcagata gtgaacattt aatacgttaa  42900
ttaaaggaat aatttacatt taagccaaac gtgaagataa actattgctc atcatccctc  42960
ttcagccgta tcctgtaggt ggtatcacct tatattctta ccaccaaaga aaatatggcc  43020
cctctcttag aaagatctta atcatttatc tgtgtatctt taggactatc cttagatcat  43080
gcctcacata ttgatgccaa agagttcttt tgtgccaatt tcataatgtg tgtcagcaca  43140
```

```
acaattctga agatttgttg gtgtctttca tgtacttgac tacaaattgc cttgccatta  43200
ctactcttct caaaggatat ctgaaattct ttttttcttt tttttttttg agatggagtc  43260
tcactgtcac ccaggctgga gtgcagtggc gtgatcttgg ctcactccat ttcccgagct  43320
caagtgattc tcatgcctca gcctcccaag tagctgggac tacaggtgtg caccaccaca  43380
ccgggctaat tttttgtatt tttagtagag acagggtttt gccatgttgg ccaggctctt  43440
gaactcccag gctcaagcga tccacccgcc tcagcctccc aaagtcctgg gattacaggc  43500
atgagccacc acgcccagcc tggatatctg aaattcttaa ctgaaattag tcaaattatc  43560
ttgtactggg gatttttttt ttaatttcaa cttttatttt tgattcaggg gatacatgca  43620
taggtttgtt acatgggtat atcatgtgat gctgaggttt ggggtacaat tgatcctgtc  43680
acccaggtag tgagcataat acccaacagt tgttcaaccc ttgcccctct cccctagtag  43740
tcctcagtgt ctattgatgc catctttatg tccacaagta acccagtgtt tagctcccac  43800
ttacaagtga gaacatgcag catttggttt tctgttcctg ggttatctca cttaggataa  43860
tggtctctgg atgcatccat gttgctgcaa aggacattat ttcattcttt tttatggttg  43920
catactgtgg attttattgg gtctttattt tgtattagca ttttaaaacc ctaaatgtga  43980
cacagtacgc atgagtgatc atgcatctca agaaatcttg aaatgttcct gtccataaag  44040
cagaattttt taagagacca tttcacagtc tcccttcccc tcactgtatc aagtgctcat  44100
ttgtgaatta ccaatttctc ttgttttgac agtggtatta ttcagcacga cttgattttc  44160
tcccttcaac aaacagaatg tgtccttaaa ccggttgaat cttcagatat gaaaatgact  44220
cagctattca ccaaagttga atcagaagat acaagtagcc tctttgacaa acttaagaag  44280
gaacctgatg ctttaacttt gctggcccca gccgctggag acacaatcat atctttagat  44340
tttggcagca acggtgagta gttatttttg ttaatcccct aaattgtgtc tgttgctaca  44400
agccccattt caactaaaca ttactttacg gtttttgttg gtaatcattt ggacattaca  44460
agctaatata tgtttatagt tttcttaaat gtatttgctt aaatattttt gccccccgtaa  44520
tttcttacca ttcttgcttt tttatactgt tggaaattgt gcttcaaagt gtccttaagg  44580
tatttcttct tcccacataa atttttcctg gctactctat ttctgtatcc tgctgtcaga  44640
ttttctccac agtttagcag agttatatgg aagtaggcat tgttgcatta aaggataaaa  44700
aagtagtcat actataacat caagcattga agatgaaaac tgcaatttta aagtagagaa  44760
cattttaatg tataaaaagg ttggtattgc cttttgtctt ttatgccata gagattaaga  44820
cgcggtatca atagtggatt gtaaaggtaa ctcagactta tggttatact atactattgt  44880
atgtaaactt tctgatgaag gaaaatttgg tgacattttg ttgtttgatg aattagacaa  44940
accttttgtg aaaaagaaca taaatttttt atatgtgaaa atccttgtgg ccgggcgcag  45000
tggctcacgc ctgtaatccc agcactttgg gaggccgagg cgggtggatc acttgaggtt  45060
aggagttcga gaccagcctg gccaccatgg tgaaaccccg tctctaccaa aaatacaaaa  45120
gttagctggg cgtggtggtg tgcgcctgta atcccagcta cttgggaggc tgaggcaggg  45180
gaattgcttg aacctgggag gcagaggttg cagtgagcca agattgcgcc attgcactcc  45240
agcctgggca acagagcaag actctgtctt gggtaaaaaa aaaaaaaaat ccttctatac  45300
tttagattga ctcatatttt ttccccacag acacagaaac tgatgaccag caacttgagg  45360
aagtaccatt atataatgat gtaatgctcc cctcacccaa cgaaaaatta cagaatataa  45420
atttggcaat gtctccatta cccaccgctg aaacgccaaa gccacttcga agtagtgctg  45480
```

-continued

```
accctgcact caatcaagaa gttgcattaa aattagaacc aaatccagag tcactggaac 45540
tttcttttac catgccccag attcaggatc agacacctag tccttccgat ggaagcacta 45600
gacaaagttc acctgaggta ggtgtcatga tataatcaga aagggacaac tttcagattt 45660
taacattcaa gaatgtattt ataagtttga ttcaaacact tatttgaacc acaaattaca 45720
tttgtgtgtg tgtttgaatt ttagcacttt aaaattattg caagagctac tgcctaacct 45780
agacctgagc acatgtttta ggctcaaaga tagtcaggaa catgggaaga aactagctta 45840
atataaacca aaaggtgaaa cgtacattgt ttctctatta tttatatcag taggacaaaa 45900
acatcttgaa tttggacatt taaagagaat agtactaagt gtgctcaagg tagctacagc 45960
ctatacctgt taccccttt agtttgtttt attgtgtttt gttttgtttt gagaaagagt 46020
ctcactatca cccaggctgg agtgcagtgg tgcaatcaca gcctcaacct cccaggctca 46080
aatgattctc ccacctcagc ctcccaagta gctgggacta caggcctgca tcaccatgcc 46140
tggctaattt tttaaccttt ttttgtgtgt gtgtgtggag ttggggttct cactatgttg 46200
ctcaggctgg ttttaaactc ctgggctcaa gcgatcctcc tgccttggcc tcccaaagta 46260
ctaggattac aggcgtgagc taccatgcct ggcccattac ccctttgagt tggagaactg 46320
tctggtagca atagacttac gagggtttaa atgggaaagg accttataaa ttctttgccc 46380
aatttagtct aatttccatc actattttga aattttgggt aagtataata tgaaaataac 46440
aagtgttaca taaaataaat acttagtaac tggtcttttt tattctggat ctgtcttgat 46500
attaattgtc ctatgaacac aaaaataatc tttaaaggct aggctggcca agacttagag 46560
atatcacaca gggctctatt tctaaatcta gaatgattcc attttagggc ttcctacatc 46620
taaaaatatg ctcaggagta gggcaactta gatctgaaca ttataacttg ataaatgagg 46680
cataaataag ctttaataag tggtaaataa ttctacatta ggtatttgtt gaataaaact 46740
gacaagctaa gagtagggga tttgacatct cacagccttg tgttgaatga atatatatcc 46800
tatgctctgg ttgcttaatt tacccagaaa aaaaaatgtt tgattcatct tggtttttat 46860
ctaacaaaag taaatctaac aaaaacgtta gaatgaggaa agcaaaattt cttgtttaga 46920
atacacagct atagtttttt gttaaacttc ttgcccagaa ctcttaaaat agtaataatg 46980
tacattcgtt caggtatatg caggtaaaat aacttaggtt tctactccca cccccgacag 47040
taacagtgag atttttaggt agctcagtca ccacaggagt gtgccttctc agttcaaagg 47100
taaattccag tgaatgtagc atctagttaa ttggtcaatt aggtaccatt gtgggatgtg 47160
aattaccaaa taggttttat tctttagaat aaggtgtttc ttttcatctc aattttgtaa 47220
atgatgttat attacatagt cagaaatata tatattggca aaattagtta ccagtataag 47280
cttcaaaatg tcactatttt cacaaatttt tttttttttt tttttttttg acatggagtc 47340
tcactctgtc gccaggctgg agtgcagtgg catgatcttg gctcactgca acctctgcct 47400
cccaggttca agtgattctc ctgcctcagc ctcctgagta gctgggatta caggcgtttg 47460
ccaccatgcc tagctaattt ttgtattttt agtagagacg aggtttcacc atgttggcca 47520
ggatggtctc gatctcttga cctcattatc cctccacctt ggcttcccaa agtgctggga 47580
ttacaggcgt gagccactga gcccggccta gttaaataaa atttgataaa cacgatggac 47640
ttggttgtgt gttttctggt ttttctgaga tctagtttga aaattctgac aactagcaaa 47700
gtatatggaa gcttcttcag gaaatagtaa acatatttct ttttacagcc taatagtccc 47760
agtgaatatt gtttttatgt ggatagtgat atggtcaatg aattcaagtt ggaattggta 47820
gaaaaacttt ttgctgaaga cacagaagca aagaacccat tttctactca ggtatatgaa 47880
```

-continued

```
cttatttgtt ttatattaaa tttcattaat ttttagtctg aagtgacttt gagtttcact  47940
tgttttttat ttataaggtg tggccattgt aaaaactcat gtatttgctg ttttaaagga  48000
cacagattta gacttggaga tgttagctcc ctatatccca atggatgatg acttccagtt  48060
acgttccttc gatcagttgt caccattaga aagcagttcc gcaagccctg aaagcgcaag  48120
tcctcaaagc acagttacag tattccagca gactcaaata caagaaccta ctgctaatgc  48180
caccactacc actgccacca ctgatgaatt aaaaacagtg acaaaagacc gtatggaaga  48240
cattaaaata ttgattgcat ctccatctcc tacccacata cataaagaaa ctactagtgc  48300
cacatcatca ccatatagag atactcaaag tcggacagcc tcaccaaaca gagcaggaaa  48360
aggagtcata gaacagacag aaaaatctca tccaagaagc cctaacgtgt tatctgtcgc  48420
tttgagtcaa aggtatttat atgtaacatt caagttatag ttcttttatt atttttgaga  48480
taaatgtatg tgatagtaca tgatttttaa acttatagca aactttctga tatatatgcc  48540
ctaacgcaaa ttcttgagaa ctcaaaaaac tttctaaatt aacctcatat atttttttctt  48600
tttctttctt tttttttttt ttgagacaga gtctcgcttt gtcgcccagg ctggagtgca  48660
atggcatggc accatctcag ctcacggcaa cctctgcctc ctgggtgcaa gagattctcc  48720
tgcctcagcc tcccgagtag ctgggattac aggcatgcac caccacgccc ggctgatttt  48780
tttggtattt ttcatagaga cagggtttct ccacgttggt caggctggtc tcaaactccc  48840
gacttcaggt gatccgcctg cctcagcctc cgaaagagct gggattacag gtgtgagcca  48900
ccatgcccgc tcctattttt tctaaaataa ttataaattc taaaattacc tatctaaatg  48960
gaggagggtc ttctgacacc tttaaaataa aatccagctc agtactgtaa atgtgtttac  49020
agaacttgtt taaagttctt acagttgttt aaatcagact agttaactac cctcactact  49080
tagatgcttc catttcttag agctcttttt taagcttatc tgaagaaaag cccttccaat  49140
ttaagggtta tttccaattg cacattccaa attgagcctt ccatcttcag cattcaatat  49200
agatatttac aggcccctct tttaaaattt tattatagtt aacttgtatt aaagttgctt  49260
ttatttttca ttacgtattt gtagaacatt agctatatat atattgcagg ctacataggt  49320
tttcaaactg tacaacagga atctaagcat gaattgttac ttctatggag ctagttcaaa  49380
caaacatatg gacatgaccc aatttttaag ttatactttc tgtatataat ttgtaagggg  49440
atttcacata ttttaagttt gaggctatag ctagaagaaa ttaagtttta tctaataagt  49500
gtgtggaaaa gggaaatgat tccttctcta ctatgtctag actaagccag atatcaatag  49560
caataggaaa gaaccactgt cgtagccaga acacatagct tttttccctg cctaacattc  49620
ccaccttgac ctagagtgct gggagaggtc ttttccctaa gcttggaaaa gacattgggg  49680
ctttagatga actcagaagt actttacatt actttattta ctgtgtcact tactcacttt  49740
tgactctgag ctccacgagg gcaatcacag tgtcttgggc attttagtga tactaatact  49800
tagctcatga cctaatgtgt agtacttcct caataaatgg ttgttgaggc agggcgcagt  49860
ggctcatcac tgtaatctca gcactttggg aggctgaagc gggtggatca cctgaggcca  49920
agagtttcag accagcctgg ccaacatggt gaaacccggt ctactaaaaa tgcaaaaatt  49980
agctgggcgt ggtggcacgt gcctgtaatc ccagctactt tgggaggttg aggcaggaga  50040
attgcttgaa ccctggaggt ggaggctgca gtgagccgag atcgtgccat tgcactccag  50100
cctgggcgag aagagtgaaa ctcggtttca aaaaaaaaaa aaaaaaaaaa agttgttgga  50160
ctgacagatg catgaataca gtagtaaaaa tgacaatcac ttataagtta cagtttacta  50220
```

-continued

```
tcagctacag aggatgggat atccagtttt ctgaacaact gttctcttgt acttgtcaaa  50280
gccaaagtgt aacaacacat caagtcactt tagcaattta tttttgagac ggagttttgc  50340
tcttgttgcc caggctggag tgcaatggcg tgatctcgga tcttggctca ccgcaactgc  50400
cgcctcgctg gttcaagcaa atctcgtgcc tcagcctccc gagtagctgg gattacaggc  50460
atgcaccacc acacccagct aattttgtat ttttagtaga gacagtgttt ctccaggttg  50520
atcaggctgg tctcaaactc ccgacctcag gtgatccacc tgcctcagcc tcccaaagtg  50580
ctgggatgac agttgtgagc cactgtgccc agctagcaac tgtttttaaa cattagttcc  50640
aatgtagtgt acactgaaaa cttttatgaa aggaatttca aaaattaaga taaaccatta  50700
aaaacgtaat tactaagtac tactactact acaatgatat ttacataata gactgagtta  50760
catttcataa agacaatata tctgtataag aatttttaaa cttccctgtc tatataatag  50820
aagttttaga gaaatttttt aaaaaccaaa gaaaactgca aaataagatc acttacctat  50880
ttggcattct caactgtctg gaacagcaag gagccattat gattatgcat ttggtttgtg  50940
gggtgtcttg aaaagtcaaa ataatgtaac aaagctgatg tactttactc attagaacaa  51000
ttcttcacaa tttaatatta attttagata tacatagttc atgtttgata accagatcaa  51060
tactgagtga aaaatagcat agtgggaaga gcaggggagg ggaggtaggg atctggagac  51120
ctagagtgta cttccatatt gcaactagtg agcagtagga ctttgagaaa gttacccaat  51180
aggcctcagg gttctaattt ataaaatggg tatgatatgc ctgccttatc tgtcttggga  51240
acttaagtaa ggttaaaatg aactaatgaa cttgaaatgt tttataaact gaaaatgcta  51300
tacgaatgtg agattgatct tgtatttcaa tagtcccaac aatatcactg cattgttata  51360
ttaggtggaa taaaaggaca atatttaact gttttgactc tacaatagtg tcaatttagt  51420
tgtgttcagc tctattttat aaaataggga tacgcatact gtagaaaatt tcctgttaaa  51480
ttaagctttg acggccaggt gctcacgcct gtaatcccag cactttggga ggccaaggtg  51540
ggcagatcac ttgcgctcag gagtttgaga ccagcctgag caacatagtg aaatcctgtc  51600
tctacaaaaa tatgtatata taaattagtc ataatcccag ctacttgaga ggctgaggtg  51660
ggaggatcac ttgattccag aggcagggct tggttgcagt aagcagagat cacgtctctg  51720
cactccagcc tggctgacag agtaagaccg tgtttcacca aaaaaaaaaa aaaaaaatta  51780
agcttttact tttaagatga taaactttag tgatcaggaa agttatctta tgtatattat  51840
attccttaat attggagaac taaagaatta tgtattttct ttaaaagcgc tcactggata  51900
ttttttttaa aaacgctata ttttcattta gaattttttt cttttcagaa ctacagttcc  51960
tgaggaagaa ctaaatccaa agatactagc tttgcagaat gctcagagaa agcgaaaaat  52020
ggaacatgat ggttcacttt ttcaagcagt aggaattgta agtatgagta gtaggttttg  52080
cttttctagc taatgtgcta tttcgtgtgt gtgtgtgtgt gtgtgtgtgt gtgtgtgttt  52140
ccacgtttct tccaaatagt aaagttatat tttcagaagt tatacattgg gtttttttac  52200
tctgtatgca ctggttttta aaaatacaaa tgtttaatac atacattctt ggtataaaaa  52260
ttccaaacaa ttccagtgta ttttgagtta aaaagtgaag ttctcccctt actccaccct  52320
gaatatcacc accaatctca ttctcttccc tttaagttac tttgccttat taaaagaact  52380
gctattggcc aggcacagtg cctcacgcct gtaatcccag cactttggga ggccaagatg  52440
aggatcactt gaggtcagga gttcgagacc agcctggcca acttggtgaa accctgtctc  52500
tactaaaaat acaaaaatta gccaggcgtg ttggtgcaca actataatcc cagccactct  52560
ggaggctgag gcaggagaat agcttgaacc cgggaggtgg aggttgcgat gagctgagat  52620
```

-continued

```
caggccactg cactccagcc tgggtaagag agtgagagtc catctcatat ttaaaaaaga  52680
actgctatgt tttggggtaa gtcaatggtg gtataataca ttctgatatt ttcaaactaa  52740
attaactgga aagtatttat agacagaatg gtcataatgg atgacaaata acttaagaaa  52800
gaattcaaaa taatttaggg tagtatttaa gaaactgcct ataatgttat taaatttaca  52860
ccaatttcaa ggtttttggt tgtttaaaaa aaaaattcaa caaactaaac ttgaaataac  52920
tttactgttt atagggaaca ttattacagc agccagacga tcatgcagct actacatcac  52980
tttcttggaa acgtgtaaaa ggatgcaaat ctagtgaaca gaatggaatg gagcaaaaga  53040
caattatttt aataccctct ggttagttta ttctttttga ccttgaacat cacaaagaca  53100
aaatacatga aacattttta tttaggagct ttaatctaag tgagaatgac tttggttcct  53160
tagcaagatt aaaaagtaaa gttgtggctg ggcgcggtgg ctcacacctg taatcccagc  53220
actttgggag gccgaggcag ccagatcatc tgaggtcagg agttggagac cagcctggcc  53280
accatggtga aaccccgtct ctactaaaaa tacaaaaatt agctgggcgt ggtggcgggc  53340
gcctgtaatc ccagctactt gggaggctga ggcatgagaa ttgcttgaac ccggaaggca  53400
gaggttgcag tgagccaaga tggcaccact gcactccagc ctgggcgaca agggtgagac  53460
tctgcctcaa aaaaaaaaaa aaaaaaaagt acagttgtat ttcatgtgat ggtcttaata  53520
cagagattaa catttcaagg tggagctttt catttttagt aattttcttt gatttctcta  53580
tgtccatgtg ctgtcaatat tgatagaagc tgaaatttgt gaacttttat gacttctttt  53640
tttttttttt tttttttgga gacagggtct cgctctgttg cccaggcctg gagtgcagtg  53700
gcatgatcat agctcactgc agtctcaaac tcctgtgctc aagctcaagc aatcatccta  53760
cctcagcctc ctgagtagct cgcactacag acatgcctca ccacacccgg ttgctttttg  53820
tagagatggg gtctcactat gttgcctagg ctggtttcaa actcctggcc tcaagtgatc  53880
ctcctgcctc agcctgtgct aggattacag gcatcagctt tgatgcccac catatttatg  53940
ccttttttcca aattgttatt tctttgtgcc tttattgtat cctgtaaaca tttctgacac  54000
agcaacagta tcactggatt atacttactt tttaacatag ttgtggtttt gccaggtaaa  54060
ctaaaaaccc ttccagaatt ttgctttatt ttctatgata cctaacacat tgtgggtgtt  54120
taataaatat tcattgacta gatgaatgta tacttaggta tctcttttgt ttttcagatt  54180
tagcatgtag actgctgggg caatcaatgg atgaaagtgg attaccacag ctgaccagtt  54240
atgattgtga agttaatgct cctatacaag gcagcagaaa cctactgcag ggtgaagaat  54300
tactcagagc tttggatcaa gttaactgag ctttttctta atttcattcc tttttttgga  54360
cactggtggc tcattaccta aagcagtcta tttatatttt ctacatctaa ttttagaagc  54420
ctggctacaa tactgcacaa acttggttag ttcaattttg atccccttttc tacttaattt  54480
acattaatgc tcttttttag tatgttcttt aatgctggat cacagacagc tcattttctc  54540
agtttttgg tatttaaacc attgcattgc agtagcatca ttttaaaaaa tgcacctttt  54600
tatttattta tttttggcta gggagtttat cccttttttcg aattattttt aagaagatgc  54660
caatataatt tttgtaagaa ggcagtaacc tttcatcatg atcataggca gttgaaaaat  54720
ttttacacct tttttttcac attttacata aataataatg ctttgccagc agtacgtggt  54780
agccacaatt gcacaatata ttttcttaaa aaataccagc agttactcat ggaatatatt  54840
ctgcgtttat aaaactagtt tttaagaaga aatttttttt ggcctatgaa attgttaaac  54900
ctggaacatg acattgttaa tcatataata atgattctta aatgctgtat ggtttattat  54960
```

-continued

```
ttaaatgggt aaagccattt acataatata gaaagatatg catatatcta gaaggtatgt  55020
ggcatttatt tggataaaat tctcaattca gagaaatcat ctgatgtttc tatagtcact  55080
ttgccagctc aaaagaaaac aataccctat gtagttgtgg aagtttatgc taatattgtg  55140
taactgatat taaacctaaa tgttctgcct accctgttgg tataaagata ttttgagcag  55200
actgtaaaca agaaaaaaaa aatcatgcat tcttagcaaa attgcctagt atgttaattt  55260
gctcaaaata caatgtttga ttttatgcac tttgtcgcta ttaacatcct tttttcatg  55320
tagatttcaa taattgagta attttagaag cattatttta ggaatatata gttgtcacag  55380
taaatatctt gttttttcta tgtacattgt acaaattttt cattcctttt gctctttgtg  55440
gttggatcta acactaactg tattgttttg ttacatcaaa taaacatctt ctgtggacca  55500
ggcccctttg atcagctttt atgttcaaat attaataata tttgcttcaa cacctccaac  55560
tcataaaatt gtttaccaac aatttaagca cttatgaaaa ttacatggta ctggttattt  55620
ctacatttat cttagtgcca tcaccttaat gtatgttgag tccctaaatg tcatgttaaa  55680
taataacaac cataatatcc cattgaaaag agtatgttgt tagaaaagaa acatcatttt  55740
taagtttctg agcctattaa aatgctcaaa cacaaaatat tagtattttt aaaatatgaa  55800
tgggatgagt gaagcagttc tcagcattat agtcacaatg ttacaaaggc tagagcttct  55860
ctgaagattt ctaatctgtt cccattaaca gattaataaa tttagacttc aaatgaataa  55920
tttgcccaag ctttaaaagt aatagatggc agaccaaaaa tgtaagctta agtttcctga  55980
ctctaaagtc aaacttagaa caaatttggt ttgtttttgt tttaatgata ctgcgtttta  56040
aaacaaagta gctttatcct ttttctcctg tatttttctt ttacaaaata gctgtatttc  56100
ttttatactg ataatctcat ttttaaaaat cagacagtgt agaaagatat tttttaaaac  56160
agaaaaatca ctatgaatcc ctgcacctac aggtacagaa aattattttt atgaacaaat  56220
tatgtaggaa gtgccagagc cttaggtcct ttaccctgag gtatatatac tgaacaaaag  56280
gaactgagcc acagatctct taggtagctc tttttatctt acaatggagg acagtgatta  56340
caattatatg aaaattttgg aacaaaagtt aatactaaga ttcagtgcaa aatttggggg  56400
gggggggggc acaggtatac ttaagcacaa acactgtgac ccaaagtgct tcaacattta  56460
gttacagata gtagtatact agaagtggta ttttagaata aagtggttgc ttagtattca  56520
caggtcacaa aacaaaaaat tattcttgta tagcaaatta gcttcagttg aaaactattt  56580
gtaaaagcag attatgtaat gaccaggagt tcaggaaaat gacttctgaa agcattgaga  56640
agggaaagcc acgttaaagg acagtacagc tggaaggaag caagtactta cccactgctc  56700
agtcactaag acaacaagct ccttggagtg ctttaagcta cggaatagca gaactggccc  56760
ttcccaattt tatgcaccgt cacaaatttc ttcataatgg ttttgtccaa ggcttataac  56820
ccaaccctgg caactataat ccttacttta tgaaacagct gtatttcttt tatactcata  56880
acccagaaaa atgagaatgt atgttctgag tataaaagaa atgtagctat tccataaaaa  56940
tacaggagaa aaagaataaa gctattttaa tttttttaat gcagtatcat taaaaaacaa  57000
accaagtttg ttctaagttt gactttagag tcaggagact taagcttaca tttctggtct  57060
gccatctatt acttttagag cttgggtaaa tcttcatttg agatctaaat gctatatata  57120
gttcattcat agcagtacca gataagggag gagtatatct atacagtata tagtcttgaa  57180
gaagtgatct aaggctcgga gcttttgagg tggccatgag tgactccaaa gtccatggag  57240
ctaaccaccc tgcagtgcta gccaatccag ttgaacatac ccttttctcc attgttaact  57300
gtttgtttaa atagcaaaca gaaggcggca atggaggtgt ggaaaactga ggatccgatg  57360
```

```
tcacttgaaa gtaatgagat cacataacat tgagggaatg tcctaagagg agtggcaggg  57420

cataaataga aatgaataaa agtgttttca agtgccattt agtgggttct gaatttgaac  57480

tagagattga gatatccagt t                                            57501
```

<210> SEQ ID NO 12
<211> LENGTH: 754
<212> TYPE: DNA
<213> ORGANISM: H. sapiens
<220> FEATURE:
<221> NAME/KEY: unsure
<222> LOCATION: 92
<223> OTHER INFORMATION: unknown
<220> FEATURE:
<221> NAME/KEY: unsure
<222> LOCATION: 181
<223> OTHER INFORMATION: unknown
<220> FEATURE:
<221> NAME/KEY: unsure
<222> LOCATION: 559
<223> OTHER INFORMATION: unknown
<220> FEATURE:
<221> NAME/KEY: unsure
<222> LOCATION: 598
<223> OTHER INFORMATION: unknown
<220> FEATURE:
<221> NAME/KEY: unsure
<222> LOCATION: 628
<223> OTHER INFORMATION: unknown
<220> FEATURE:
<221> NAME/KEY: unsure
<222> LOCATION: 678
<223> OTHER INFORMATION: unknown
<220> FEATURE:
<221> NAME/KEY: unsure
<222> LOCATION: 687
<223> OTHER INFORMATION: unknown
<220> FEATURE:
<221> NAME/KEY: unsure
<222> LOCATION: 694
<223> OTHER INFORMATION: unknown
<220> FEATURE:
<221> NAME/KEY: unsure
<222> LOCATION: 718
<223> OTHER INFORMATION: unknown
<221> NAME/KEY: unsure
<222> LOCATION: 748
<223> OTHER INFORMATION: unknown
<223> OTHER INFORMATION:

<400> SEQUENCE: 12

```
ccctgacgct gcctcagctc ctcagtgcac agtgctgcct cgtctgaggg gacaggagga     60

tcaccctctt cgtcgcttcg gccagtgtgt cnggctgggc cctgacaagc cacctgagga    120

gaggctcgga gccgggcccg gaccccggcg attgccgccc gcttctctct agtctcacga    180

ngggtttccc gcctcgcacc cccacctctg gacttgcctt tccttctctt ctccgcgtgt    240

ggagggagcc agcgcttatg ccggagcgag cctgggggcc gcccgccgtg aagacatcgc    300

ggggaccgat tcaccatgga gggcgccggc ggcgcgaacg acaagaaaaa gataagttct    360

gaacgtcgaa aagaaaagtc tcgagatgca gccagatctc ggcgaagtaa agaatctgaa    420

gtttttttatg agcttgctca tcagttgcca cttccacata atgtgagttc gcatcttgat    480

aaggcctctg tgatgaggct taccatcagc tatttgcgtg tgaggaaact tctggatgct    540

ggtgatttgg atattgaana tgacatgaaa gcacagatga attgctttta tttgaaancc    600

ttgggatggt tttgttatgg ttctcccnca tgatggtgac atgattttac atttcttgat    660

aatgttgaaa caaatacntt gggattnact tcanttttga aacttaactg ggaaacantg    720
```

-continued tgttttgatt tttactccat cccatgtnaa ccat 754

<210> SEQ ID NO 13
<211> LENGTH: 3551
<212> TYPE: DNA
<213> ORGANISM: H. sapiens
<220> FEATURE:
<221> NAME/KEY: CDS
<222> LOCATION: (29)...(2236)

<400> SEQUENCE: 13
gtgaagacat cgcggggacc gattcacc atg gag ggc gcc ggc ggc gcg aac 52
Met Glu Gly Ala Gly Gly Ala Asn
1 5 gac aag aaa aag ata agt tct gaa cgt cga aaa gaa aag tct cga gat 100
Asp Lys Lys Lys Ile Ser Ser Glu Arg Arg Lys Glu Lys Ser Arg Asp
10 15 20 gca gcc aga tct cgg cga agt aaa gaa tct gaa gtt ttt tat gag ctt 148
Ala Ala Arg Ser Arg Arg Ser Lys Glu Ser Glu Val Phe Tyr Glu Leu
25 30 35 40 gct cat cag ttg cca ctt cca cat aat gtg agt tcg cat ctt gat aag 196
Ala His Gln Leu Pro Leu Pro His Asn Val Ser Ser His Leu Asp Lys
45 50 55 gcc tct gtg atg agg ctt acc atc agc tat ttg cgt gtg agg aaa ctt 244
Ala Ser Val Met Arg Leu Thr Ile Ser Tyr Leu Arg Val Arg Lys Leu
60 65 70 ctg gat gct ggt gat ttg gat att gaa gat gac atg aaa gca cag atg 292
Leu Asp Ala Gly Asp Leu Asp Ile Glu Asp Asp Met Lys Ala Gln Met
75 80 85 aat tgc ttt tat ttg aaa gcc ttg gat ggt ttt gtt atg gtt ctc aca 340
Asn Cys Phe Tyr Leu Lys Ala Leu Asp Gly Phe Val Met Val Leu Thr
90 95 100 gat gat ggt gac atg att tac att tct gat aat gtg aac aaa tac atg 388
Asp Asp Gly Asp Met Ile Tyr Ile Ser Asp Asn Val Asn Lys Tyr Met
105 110 115 120 gga tta act cag ttt gaa cta act gga cac agt gtg ttt gat ttt act 436
Gly Leu Thr Gln Phe Glu Leu Thr Gly His Ser Val Phe Asp Phe Thr
125 130 135 cat cca tgt gac cat gag gaa atg aga gaa atg ctt aca cac aga aat 484
His Pro Cys Asp His Glu Glu Met Arg Glu Met Leu Thr His Arg Asn
140 145 150 ggc ctt gtg aaa aag ggt aaa gaa caa aac aca cag cga agc ttt ttt 532
Gly Leu Val Lys Lys Gly Lys Glu Gln Asn Thr Gln Arg Ser Phe Phe
155 160 165 ctc aga atg aag tgt acc cta act agc cga gga aga act atg aac ata 580
Leu Arg Met Lys Cys Thr Leu Thr Ser Arg Gly Arg Thr Met Asn Ile
170 175 180 aag tct gca aca tgg aag gta ttg cac tgc aca ggc cac att cac gta 628
Lys Ser Ala Thr Trp Lys Val Leu His Cys Thr Gly His Ile His Val
185 190 195 200 tat gat acc aac agt aac caa cct cag tgt ggg tat aag aaa cca cct 676
Tyr Asp Thr Asn Ser Asn Gln Pro Gln Cys Gly Tyr Lys Lys Pro Pro
205 210 215 atg acc tgc ttg gtg ctg att tgt gaa ccc att cct cac cca tca aat 724
Met Thr Cys Leu Val Leu Ile Cys Glu Pro Ile Pro His Pro Ser Asn
220 225 230 att gaa att cct tta gat agc aag act ttc ctc agt cga cac agc ctg 772
Ile Glu Ile Pro Leu Asp Ser Lys Thr Phe Leu Ser Arg His Ser Leu
235 240 245 gat atg aaa ttt tct tat tgt gat gaa aga att acc gaa ttg atg gga 820
Asp Met Lys Phe Ser Tyr Cys Asp Glu Arg Ile Thr Glu Leu Met Gly -continued

```
    250                 255                 260

tat gag cca gaa gaa ctt tta ggc cgc tca att tat gaa tat tat cat      868
Tyr Glu Pro Glu Glu Leu Leu Gly Arg Ser Ile Tyr Glu Tyr Tyr His
265                 270                 275                 280

gct ttg gac tct gat cat ctg acc aaa act cat cat gat atg ttt act      916
Ala Leu Asp Ser Asp His Leu Thr Lys Thr His His Asp Met Phe Thr
                285                 290                 295

aaa gga caa gtc acc aca gga cag tac agg atg ctt gcc aaa aga ggt      964
Lys Gly Gln Val Thr Thr Gly Gln Tyr Arg Met Leu Ala Lys Arg Gly
            300                 305                 310

gga tat gtc tgg gtt gaa act caa gca act gtc ata tat aac acc aag     1012
Gly Tyr Val Trp Val Glu Thr Gln Ala Thr Val Ile Tyr Asn Thr Lys
        315                 320                 325

aat tct caa cca cag tgc att gta tgt gtg aat tac gtt gtg agt ggt     1060
Asn Ser Gln Pro Gln Cys Ile Val Cys Val Asn Tyr Val Val Ser Gly
    330                 335                 340

att att cag cac gac ttg att ttc tcc ctt caa caa aca gaa tgt gtc     1108
Ile Ile Gln His Asp Leu Ile Phe Ser Leu Gln Gln Thr Glu Cys Val
345                 350                 355                 360

ctt aaa ccg gtt gaa tct tca gat atg aaa atg act cag cta ttc acc     1156
Leu Lys Pro Val Glu Ser Ser Asp Met Lys Met Thr Gln Leu Phe Thr
                365                 370                 375

aaa gtt gaa tca gaa gat aca agt agc ctc ttt gac aaa ctt aag aag     1204
Lys Val Glu Ser Glu Asp Thr Ser Ser Leu Phe Asp Lys Leu Lys Lys
            380                 385                 390

gaa cct gat gct tta act ttg ctg gcc cca gcc gct gga gac aca atc     1252
Glu Pro Asp Ala Leu Thr Leu Leu Ala Pro Ala Ala Gly Asp Thr Ile
        395                 400                 405

ata tct tta gat ttt ggc agc aac gac aca gaa act gat gac cag caa     1300
Ile Ser Leu Asp Phe Gly Ser Asn Asp Thr Glu Thr Asp Asp Gln Gln
    410                 415                 420

ctt gag gaa gta cca tta tat aat gat gta atg ctc ccc tca ccc aac     1348
Leu Glu Glu Val Pro Leu Tyr Asn Asp Val Met Leu Pro Ser Pro Asn
425                 430                 435                 440

gaa aaa tta cag aat ata aat ttg gca atg tct cca tta ccc acc gct     1396
Glu Lys Leu Gln Asn Ile Asn Leu Ala Met Ser Pro Leu Pro Thr Ala
                445                 450                 455

gaa acg cca aag cca ctt cga agt agt gct gac cct gca ctc aat caa     1444
Glu Thr Pro Lys Pro Leu Arg Ser Ser Ala Asp Pro Ala Leu Asn Gln
            460                 465                 470

gaa gtt gca tta aaa tta gaa cca aat cca gag tca ctg gaa ctt tct     1492
Glu Val Ala Leu Lys Leu Glu Pro Asn Pro Glu Ser Leu Glu Leu Ser
        475                 480                 485

ttt acc atg ccc cag att cag gat cag aca cct agt cct tcc gat gga     1540
Phe Thr Met Pro Gln Ile Gln Asp Gln Thr Pro Ser Pro Ser Asp Gly
    490                 495                 500

agc act aga caa agt tca cct gag cct aat agt ccc agt gaa tat tgt     1588
Ser Thr Arg Gln Ser Ser Pro Glu Pro Asn Ser Pro Ser Glu Tyr Cys
505                 510                 515                 520

ttt tat gtg gat agt gat atg gtc aat gaa ttc aag ttg gaa ttg gta     1636
Phe Tyr Val Asp Ser Asp Met Val Asn Glu Phe Lys Leu Glu Leu Val
                525                 530                 535

gaa aaa ctt ttt gct gaa gac aca gaa gca aag aac cca ttt tct act     1684
Glu Lys Leu Phe Ala Glu Asp Thr Glu Ala Lys Asn Pro Phe Ser Thr
            540                 545                 550

cag gac aca gat tta gac ttg gag atg tta gct ccc tat atc cca atg     1732
Gln Asp Thr Asp Leu Asp Leu Glu Met Leu Ala Pro Tyr Ile Pro Met
        555                 560                 565

gat gat gac ttc cag tta cgt tcc ttc gat cag ttg tca cca tta gaa     1780
```

-continued

```
Asp Asp Asp Phe Gln Leu Arg Ser Phe Asp Gln Leu Ser Pro Leu Glu
    570                 575                 580

agc agt tcc gca agc cct gaa agc gca agt cct caa agc aca gtt aca     1828
Ser Ser Ser Ala Ser Pro Glu Ser Ala Ser Pro Gln Ser Thr Val Thr
585                 590                 595                 600

gta ttc cag cag act caa ata caa gaa cct act gct aat gcc acc act     1876
Val Phe Gln Gln Thr Gln Ile Gln Glu Pro Thr Ala Asn Ala Thr Thr
                605                 610                 615

acc act gcc acc act gat gaa tta aaa aca gtg aca aaa gac cgt atg     1924
Thr Thr Ala Thr Thr Asp Glu Leu Lys Thr Val Thr Lys Asp Arg Met
            620                 625                 630

gaa gac att aaa ata ttg att gca tct cca tct cct acc cac ata cat     1972
Glu Asp Ile Lys Ile Leu Ile Ala Ser Pro Ser Pro Thr His Ile His
        635                 640                 645

aaa gaa act act agt gcc aca tca tca cca tat aga gat act caa agt     2020
Lys Glu Thr Thr Ser Ala Thr Ser Ser Pro Tyr Arg Asp Thr Gln Ser
    650                 655                 660

cgg aca gcc tca cca aac aga gca gga aaa gga gtc ata gaa cag aca     2068
Arg Thr Ala Ser Pro Asn Arg Ala Gly Lys Gly Val Ile Glu Gln Thr
665                 670                 675                 680

gaa aaa tct cat cca aga agc cct aac gtg tta tct gtc gct ttg agt     2116
Glu Lys Ser His Pro Arg Ser Pro Asn Val Leu Ser Val Ala Leu Ser
                685                 690                 695

caa aga act aca gtt cct gag gaa gaa cta aat cca aag ata cta gct     2164
Gln Arg Thr Thr Val Pro Glu Glu Glu Leu Asn Pro Lys Ile Leu Ala
            700                 705                 710

ttg cag aat gct cag aga aag cga aaa atg gaa cat gat ggt tca ctt     2212
Leu Gln Asn Ala Gln Arg Lys Arg Lys Met Glu His Asp Gly Ser Leu
        715                 720                 725

ttt caa gca gta gga att att tag catgtagact gctggggcaa tcaatggatg    2266
Phe Gln Ala Val Gly Ile Ile
    730                 735

aaagtggatt accacagctg accagttatg attgtgaagt taatgctcct atacaaggca   2326

gcagaaacct actgcagggt gaagaattac tcagagcttt ggatcaagtt aactgagctt   2386

tttcttaatt tcattccttt ttttggacac tggtggctca ctacctaaag cagtctattt   2446

atattttcta catctaattt tagaagcctg gctacaatac tgcacaaact tggttagttc   2506

aatttttgat cccctttcta cttaatttac attaatgctc ttttttagta tgttctttaa   2566

tgctggatca cagacagctc attttctcag ttttttggta tttaaaccat tgcattgcag   2626

tagcatcatt ttaaaaaatg caccttttta tttatttatt tttggctagg gagtttatcc   2686

ctttttcgaa ttatttttaa gaagatgcca atataatttt tgtaagaagg cagtaacctt   2746

tcatcatgat catagggcagt tgaaaaattt ttacaccttt tttttcacat tttacataaa   2806

taataatgct ttgccagcag tacgtggtag ccacaattgc acaatatatt ttcttaaaaa   2866

ataccagcag ttactcatgg aatatattct gcgtttataa aactagtttt taagaagaaa   2926

ttttttttgg cctatgaaat tgttaaacct ggaacatgac attgttaatc atataataat   2986

gattcttaaa tgctgtatgg tttattattt aaatgggtaa agccatttac ataatataga   3046

aagatatgca tatatctaga aggtatgtgg catttatttg gataaaattc tcaattcaga   3106

gaaatcatct gatgtttcta tagtcacttt gccagctcaa aagaaaacaa taccctatgt   3166

agttgtggaa gtttatgcta atattgtgta actgatatta aacctaaatg ttctgcctac   3226

cctgttggta taaagatatt ttgagcagac tgtaaacaag aaaaaaaaaa tcatgcattc   3286

ttagcaaaat tgcctagtat gttaatttgc tcaaaataca atgtttgatt ttatgcactt   3346
```

-continued

```
tgtcgctatt aacatccttt ttttcatgta gatttcaata attgagtaat tttagaagca   3406

ttattttagg aatatatagt tgtcacagta aatatcttgt tttttctatg tacattgtac   3466

aaatttttca ttccttttgc tctttgtggt tggatctaac actaactgta ttgttttgtt   3526

acatcaaata aacatcttct gtgga                                         3551


<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14

aaagtgatgt agtagctgca                                                20


<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15

ggtatcatat acgtgaatgt                                                20


<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16

taccacgtac tgctggcaaa                                                20


<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17

tgtgctttga ggacttgcgc                                                20


<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18

gaaatgtaaa tcatgtcacc                                                20


<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19

tcaaagaggc tacttgtatc                                                20
```

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ttaatgcaac ttcttgattg 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
atcattatta tatgattaac 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gaaaggcaag tccagaggtg 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
taaactccct agccaaaaat 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
cattagcagt aggttcttgt 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gatcatgatg aaaggttact 20

<210> SEQ ID NO 26
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 26
aaatttcata tccaggctgt 20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
agtttcctca cacgcaaata 20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
actgatcgaa ggaacgtaac 20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
cgctttctct gagcattctg 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
aaatcaaaca cactgtgtcc 20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tcctttagta aacatatcat 20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
caaagttaaa gcatcaggtt 20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ctagtgcttc catcggaagg 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
aatgccacat accttctaga 20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tcgtgagact agagagaagc 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
atgaaaggtt actgccttct 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tcagcaccaa gcaggtcata 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
aagtttgtgc agtattgtag 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ctgagcattc tgcaaagcta 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ttcagattct ttacttcgcc 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gataacacgt tagggcttct 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
tcaaagcgac agataacacg 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
caaagcatga taatattcat 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ccatcatctg tgagaaccat 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
atatggtgat gatgtggcac 20

<210> SEQ ID NO 46
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 46

ctcctcaggt ggcttgtcag                                                  20


<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47

tgagctgtct gtgatccagc                                                  20


<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48

agataacacg ttagggcttc                                                  20


<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49

catggtgaat cggtccccgc                                                  20


<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50

tgttatatat gacagttgct                                                  20


<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51

ccttatcaag atgcgaactc                                                  20


<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
```

-continued ccaaatcacc agcatccaga 20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
aactgagtta atcccatgta 20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ttagttcaaa ctgagttaat 20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
aggccatttc tgtgtgtaag 20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ctatctaaag gaatttcaat 20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
cccatcaatt cggtaattct 20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tatcatgatg agttttggtc 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
aataatacca ctcacaacgt 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
caactttggt gaatagctga 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
agtgactctg gatttggttc 20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
catctccaag tctaaatctg 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ctaatggtga caactgatcg 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
cactgttttt aattcatcag 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ataatgttcc aattcctact 20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
agaaaaagct cagttaactt 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
attgtagcca ggcttctaaa 20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
atcttcttaa aaataattcg 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tgtgcaattg tggctaccac 20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
aacaatgtca tgttccaggt 20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gctggcaaag tgactataga 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ttccacagaa gatgtttatt 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tttttccaca gaagatgttt 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tagagctaaa cgatctagaa 20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
taactctttc tggccttgaa 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
attggcccta acagaaaatc 20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
agaacttatc ctacttaaca 20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gtttccctcg tgttgctcag 20

<210> SEQ ID NO 79

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79

ttgtacttac tatcatgatg                                                    20


<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80

acttacttac ctcacaacgt                                                    20


<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81

aatctgtgtc ctttaaaaca                                                    20


<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82

tgtgcactga ggagctgagg                                                    20


<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83

acgttcagaa cttatctttt                                                    20


<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84

catgctaaat aattcctact                                                    20


<210> SEQ ID NO 85
<211> LENGTH: 20
<212> TYPE: DNA
<213> ORGANISM: H. sapiens
<220> FEATURE:

<400> SEQUENCE: 85
```

-continued tgcagctact acatcacttt 20

<210> SEQ ID NO 86
<211> LENGTH: 20
<212> TYPE: DNA
<213> ORGANISM: H. sapiens
<220> FEATURE:

<400> SEQUENCE: 86
acattcacgt atatgatacc 20

<210> SEQ ID NO 87
<211> LENGTH: 20
<212> TYPE: DNA
<213> ORGANISM: H. sapiens
<220> FEATURE:

<400> SEQUENCE: 87
gcgcaagtcc tcaaagcaca 20

<210> SEQ ID NO 88
<211> LENGTH: 20
<212> TYPE: DNA
<213> ORGANISM: H. sapiens
<220> FEATURE:

<400> SEQUENCE: 88
ggtgacatga tttacatttc 20

<210> SEQ ID NO 89
<211> LENGTH: 20
<212> TYPE: DNA
<213> ORGANISM: H. sapiens
<220> FEATURE:

<400> SEQUENCE: 89
gatacaagta gcctctttga 20

<210> SEQ ID NO 90
<211> LENGTH: 20
<212> TYPE: DNA
<213> ORGANISM: H. sapiens
<220> FEATURE:

<400> SEQUENCE: 90
caatcaagaa gttgcattaa 20

<210> SEQ ID NO 91
<211> LENGTH: 20
<212> TYPE: DNA
<213> ORGANISM: H. sapiens
<220> FEATURE:

<400> SEQUENCE: 91
gttaatcata taataatgat 20

<210> SEQ ID NO 92
<211> LENGTH: 20
<212> TYPE: DNA
<213> ORGANISM: H. sapiens
<220> FEATURE:

<400> SEQUENCE: 92
cacctctgga cttgcctttc 20

<210> SEQ ID NO 93
<211> LENGTH: 20
<212> TYPE: DNA
<213> ORGANISM: H. sapiens
<220> FEATURE:

<400> SEQUENCE: 93
atttttggct agggagttta 20

<210> SEQ ID NO 94
<211> LENGTH: 20
<212> TYPE: DNA
<213> ORGANISM: H. sapiens
<220> FEATURE:

<400> SEQUENCE: 94
acaagaacct actgctaatg 20

<210> SEQ ID NO 95
<211> LENGTH: 20
<212> TYPE: DNA
<213> ORGANISM: H. sapiens
<220> FEATURE:

<400> SEQUENCE: 95
agtaaccttt catcatgatc 20

<210> SEQ ID NO 96
<211> LENGTH: 20
<212> TYPE: DNA
<213> ORGANISM: H. sapiens
<220> FEATURE:

<400> SEQUENCE: 96
acagcctgga tatgaaattt 20

<210> SEQ ID NO 97
<211> LENGTH: 20
<212> TYPE: DNA
<213> ORGANISM: H. sapiens
<220> FEATURE:

<400> SEQUENCE: 97
gttacgttcc ttcgatcagt 20

<210> SEQ ID NO 98
<211> LENGTH: 20
<212> TYPE: DNA
<213> ORGANISM: H. sapiens
<220> FEATURE:

<400> SEQUENCE: 98
cagaatgctc agagaaagcg 20

<210> SEQ ID NO 99
<211> LENGTH: 20
<212> TYPE: DNA
<213> ORGANISM: H. sapiens
<220> FEATURE:

<400> SEQUENCE: 99
ggacacagtg tgtttgattt 20

<210> SEQ ID NO 100

<211> LENGTH: 20
<212> TYPE: DNA
<213> ORGANISM: H. sapiens
<220> FEATURE:

<400> SEQUENCE: 100
atgatatgtt tactaaagga 20

<210> SEQ ID NO 101
<211> LENGTH: 20
<212> TYPE: DNA
<213> ORGANISM: H. sapiens
<220> FEATURE:

<400> SEQUENCE: 101
aacctgatgc tttaactttg 20

<210> SEQ ID NO 102
<211> LENGTH: 20
<212> TYPE: DNA
<213> ORGANISM: H. sapiens
<220> FEATURE:

<400> SEQUENCE: 102
gcttctctct agtctcacga 20

<210> SEQ ID NO 103
<211> LENGTH: 20
<212> TYPE: DNA
<213> ORGANISM: H. sapiens
<220> FEATURE:

<400> SEQUENCE: 103
agaaggcagt aacctttcat 20

<210> SEQ ID NO 104
<211> LENGTH: 20
<212> TYPE: DNA
<213> ORGANISM: H. sapiens
<220> FEATURE:

<400> SEQUENCE: 104
ggcgaagtaa agaatctgaa 20

<210> SEQ ID NO 105
<211> LENGTH: 20
<212> TYPE: DNA
<213> ORGANISM: H. sapiens
<220> FEATURE:

<400> SEQUENCE: 105
agaagcccta acgtgttatc 20

<210> SEQ ID NO 106
<211> LENGTH: 20
<212> TYPE: DNA
<213> ORGANISM: H. sapiens
<220> FEATURE:

<400> SEQUENCE: 106
cgtgttatct gtcgctttga 20

<210> SEQ ID NO 107
<211> LENGTH: 20
<212> TYPE: DNA

<213> ORGANISM: H. sapiens
<220> FEATURE:

<400> SEQUENCE: 107
atgaatatta tcatgctttg 20

<210> SEQ ID NO 108
<211> LENGTH: 20
<212> TYPE: DNA
<213> ORGANISM: H. sapiens
<220> FEATURE:

<400> SEQUENCE: 108
atggttctca cagatgatgg 20

<210> SEQ ID NO 109
<211> LENGTH: 20
<212> TYPE: DNA
<213> ORGANISM: H. sapiens
<220> FEATURE:

<400> SEQUENCE: 109
gtgccacatc atcaccatat 20

<210> SEQ ID NO 110
<211> LENGTH: 20
<212> TYPE: DNA
<213> ORGANISM: H. sapiens
<220> FEATURE:

<400> SEQUENCE: 110
gctggatcac agacagctca 20

<210> SEQ ID NO 111
<211> LENGTH: 20
<212> TYPE: DNA
<213> ORGANISM: H. sapiens
<220> FEATURE:

<400> SEQUENCE: 111
gaagccctaa cgtgttatct 20

<210> SEQ ID NO 112
<211> LENGTH: 20
<212> TYPE: DNA
<213> ORGANISM: H. sapiens
<220> FEATURE:

<400> SEQUENCE: 112
gcggggaccg attcaccatg 20

<210> SEQ ID NO 113
<211> LENGTH: 20
<212> TYPE: DNA
<213> ORGANISM: H. sapiens
<220> FEATURE:

<400> SEQUENCE: 113
agcaactgtc atatataaca 20

<210> SEQ ID NO 114
<211> LENGTH: 20
<212> TYPE: DNA
<213> ORGANISM: H. sapiens
<220> FEATURE:

<400> SEQUENCE: 114
gagttcgcat cttgataagg 20

<210> SEQ ID NO 115
<211> LENGTH: 20
<212> TYPE: DNA
<213> ORGANISM: H. sapiens
<220> FEATURE:

<400> SEQUENCE: 115
tacatgggat taactcagtt 20

<210> SEQ ID NO 116
<211> LENGTH: 20
<212> TYPE: DNA
<213> ORGANISM: H. sapiens
<220> FEATURE:

<400> SEQUENCE: 116
cttacacaca gaaatggcct 20

<210> SEQ ID NO 117
<211> LENGTH: 20
<212> TYPE: DNA
<213> ORGANISM: H. sapiens
<220> FEATURE:

<400> SEQUENCE: 117
agaattaccg aattgatggg 20

<210> SEQ ID NO 118
<211> LENGTH: 20
<212> TYPE: DNA
<213> ORGANISM: H. sapiens
<220> FEATURE:

<400> SEQUENCE: 118
gaccaaaact catcatgata 20

<210> SEQ ID NO 119
<211> LENGTH: 20
<212> TYPE: DNA
<213> ORGANISM: H. sapiens
<220> FEATURE:

<400> SEQUENCE: 119
acgttgtgag tggtattatt 20

<210> SEQ ID NO 120
<211> LENGTH: 20
<212> TYPE: DNA
<213> ORGANISM: H. sapiens
<220> FEATURE:

<400> SEQUENCE: 120
tcagctattc accaaagttg 20

<210> SEQ ID NO 121
<211> LENGTH: 20
<212> TYPE: DNA
<213> ORGANISM: H. sapiens
<220> FEATURE:

<400> SEQUENCE: 121
gaaccaaatc cagagtcact 20

<210> SEQ ID NO 122
<211> LENGTH: 20
<212> TYPE: DNA
<213> ORGANISM: H. sapiens
<220> FEATURE:

<400> SEQUENCE: 122
cgatcagttg tcaccattag 20

<210> SEQ ID NO 123
<211> LENGTH: 20
<212> TYPE: DNA
<213> ORGANISM: H. sapiens
<220> FEATURE:

<400> SEQUENCE: 123
ctgatgaatt aaaaacagtg 20

<210> SEQ ID NO 124
<211> LENGTH: 20
<212> TYPE: DNA
<213> ORGANISM: H. sapiens
<220> FEATURE:

<400> SEQUENCE: 124
aagttaactg agctttttct 20

<210> SEQ ID NO 125
<211> LENGTH: 20
<212> TYPE: DNA
<213> ORGANISM: H. sapiens
<220> FEATURE:

<400> SEQUENCE: 125
tttagaagcc tggctacaat 20

<210> SEQ ID NO 126
<211> LENGTH: 20
<212> TYPE: DNA
<213> ORGANISM: H. sapiens
<220> FEATURE:

<400> SEQUENCE: 126
gtggtagcca caattgcaca 20

<210> SEQ ID NO 127
<211> LENGTH: 20
<212> TYPE: DNA
<213> ORGANISM: H. sapiens
<220> FEATURE:

<400> SEQUENCE: 127
acctggaaca tgacattgtt 20

<210> SEQ ID NO 128
<211> LENGTH: 20
<212> TYPE: DNA
<213> ORGANISM: H. sapiens
<220> FEATURE:

<400> SEQUENCE: 128
tctatagtca ctttgccagc 20

-continued

```
<210> SEQ ID NO 129
<211> LENGTH: 20
<212> TYPE: DNA
<213> ORGANISM: H. sapiens
<220> FEATURE:

<400> SEQUENCE: 129

ttctagatcg tttagctcta                                                20


<210> SEQ ID NO 130
<211> LENGTH: 20
<212> TYPE: DNA
<213> ORGANISM: H. sapiens
<220> FEATURE:

<400> SEQUENCE: 130

ttcaaggcca gaaagagtta                                                20


<210> SEQ ID NO 131
<211> LENGTH: 20
<212> TYPE: DNA
<213> ORGANISM: H. sapiens
<220> FEATURE:

<400> SEQUENCE: 131

ctgagcaaca cgagggaaac                                                20


<210> SEQ ID NO 132
<211> LENGTH: 20
<212> TYPE: DNA
<213> ORGANISM: H. sapiens
<220> FEATURE:

<400> SEQUENCE: 132

aaaagataag ttctgaacgt                                                20
```